US010975162B2

(12) United States Patent
Pulé et al.

(10) Patent No.: US 10,975,162 B2
(45) Date of Patent: Apr. 13, 2021

(54) CHIMERIC ANTIGEN RECEPTOR

(71) Applicant: AUTOLUS LIMITED, London (GB)

(72) Inventors: Martin Pulé, London (GB); John Anderson, London (GB); Simon Thomas, London (GB)

(73) Assignee: AUTOLUS LIMITED, London (GB)

( * ) Notice: Subject to any disclaimer, the term of this patent is extended or adjusted under 35 U.S.C. 154(b) by 13 days.

(21) Appl. No.: 15/123,331

(22) PCT Filed: Mar. 6, 2015

(86) PCT No.: PCT/GB2015/050649
§ 371 (c)(1),
(2) Date: Sep. 2, 2016

(87) PCT Pub. No.: WO2015/132604
PCT Pub. Date: Sep. 11, 2015

(65) Prior Publication Data
US 2017/0066838 A1 Mar. 9, 2017

(30) Foreign Application Priority Data
Mar. 6, 2014 (GB) ..................................... 1403972

(51) Int. Cl.
| C07K 16/30 | (2006.01) |
| C07K 14/725 | (2006.01) |
| C07K 14/705 | (2006.01) |
| A61K 35/17 | (2015.01) |
| A61K 38/17 | (2006.01) |
| A61K 39/395 | (2006.01) |
| C12N 15/85 | (2006.01) |
| A61K 39/00 | (2006.01) |

(52) U.S. Cl.
CPC .......... C07K 16/3084 (2013.01); A61K 35/17 (2013.01); A61K 38/179 (2013.01); A61K 38/1774 (2013.01); A61K 39/39558 (2013.01); C07K 14/7051 (2013.01); C07K 14/70517 (2013.01); C07K 14/70521 (2013.01); C07K 14/70578 (2013.01); C12N 15/85 (2013.01); A61K 2039/505 (2013.01); C07K 2317/21 (2013.01); C07K 2317/24 (2013.01); C07K 2317/52 (2013.01); C07K 2317/53 (2013.01); C07K 2317/565 (2013.01); C07K 2317/622 (2013.01); C07K 2317/73 (2013.01); C07K 2319/00 (2013.01); C07K 2319/03 (2013.01); C07K 2319/20 (2013.01); C07K 2319/30 (2013.01); C12N 2510/00 (2013.01)

(58) Field of Classification Search
None
See application file for complete search history.

(56) References Cited

U.S. PATENT DOCUMENTS

2013/0216528 A1 8/2013 Cheung et al.
2015/0093401 A1 4/2015 Pule et al.

FOREIGN PATENT DOCUMENTS

| CL | 201601135 | 5/2016 | |
| CL | 201702413 | 9/2017 | |
| CN | 103145849 A | 6/2013 | |
| RU | 2366664 C2 | 9/2009 | |
| RU | 2462476 C2 | 9/2012 | |
| WO | WO-01/23573 A1 | 4/2001 | |
| WO | WO-0123573 A1 * | 4/2001 | ......... C07K 16/3084 |
| WO | WO-2012/033885 A1 | 3/2012 | |
| WO | WO-2012/079000 A1 | 6/2012 | |
| WO | WO-2013/040371 A2 | 3/2013 | |
| WO | WO-2013/040557 A2 | 3/2013 | |
| WO | WO-2015/052538 A1 | 4/2015 | |
| WO | WO-2015/075469 A1 | 5/2015 | |
| WO | WO-2015/075470 A1 | 5/2015 | |
| WO | WO-2015/132598 A1 | 9/2015 | |
| WO | WO-2016/030691 A1 | 3/2016 | |
| WO | WO-2016/138038 A1 | 9/2016 | |
| WO | WO-2016/151315 A1 | 9/2016 | |

OTHER PUBLICATIONS

Tur et al., An Anti-GD2 Single Chain Fv Selected by Phage Display and Fused to Pseudomonas Exotoxin A Develops Specific Cytotoxic Activity Against Neuroblastoma Derived Cell Lines. International Journal of Molecular Medicine, 2001. 8:579-584.*
Rudikoff, et al., Single Amino Acid Substitution Altering Antigen-binding Specificity, PNAS, 1982. (79):1979-1983.*
Shirasu et al. Functional Design of Chimeric T-Cell Antigen Receptors for Adoptive Immunotherapy of Caner: Architecture and Outcomes. Anticancer Research, 2012. 32:2377-2384.*
Zhong, S. et al., PNAS, 2013, vol. 110: pp. 6973-6978.*
Schmid, D. et al, J. Immunol . . . , 2010, vol. 184: pp. 4936-4946.*
Esser et al., NK cells engineered to express a GD2-specific antigen receptor display built-in ADCC-like activity against tumour cells of neuroectodermal origin. *J. Cell. Mol. Med.* 16: 569-81 (2012).
Nakamura et al., Construction of humanized anti-ganglioside monoclonal antibodies with potent immune effector functions. *Cancer Immunol. Immunother.* 50(5): 275-84 (2001).
Yvon et al., Immunotherapy of metastatic melanoma using genetically engineered GD2-specific T cells. *Clin. Cancer Res.* 15: 5852-60 (2009).
Auten et al., "Effect of scaffold Attachment Region on Transgene Expression in Retrovirus Vector-Transduced Primary T Cells and Macrophages," Human Gene Therapy, 10(8):1389-1399 (1999).
Cooper et al., "Enhanced Transgene Expression in quiescent and Activated Human CD8+ T Cells," Human Gene Therapy, 15:648-658 (2004).

(Continued)

*Primary Examiner* — Michael D Burkhart
(74) *Attorney, Agent, or Firm* — Marshall, Gerstein & Borun LLP

(57) ABSTRACT

The present invention relates to chimeric antigen receptor (CAR) which binds the cancer antigen disialoganglioside (GD2). T cells expressing such a CAR are useful in the treatment of cancerous diseases such as neuroblastoma.

17 Claims, 12 Drawing Sheets

Specification includes a Sequence Listing.

(56) References Cited

OTHER PUBLICATIONS

Curran et al., "Chimeric Antigen Receptors for T Cell Immunotherapy: Current Understanding and Future Direction", Journal of Gene Medicine 14(6):405-415 (2012).

International Search Report and Written Opinion from International Application No. PCT/GB2015/050649 dated Jun. 2, 2015.

Kim, "Improved Expression Vector Activity Using Insulators and Scaffold/Matrix-Attachment Regions for Enhancing Recombinant Protein Production," Bioprocess International, Suppl. pp. 24-31 (2006).

Straathof et al., "Optimized Anti-GD2/Suicide Gene Cassette and Scale-Up for a Next Generation GD2 Chimeric Antigen Receptor Study for Neuroblastoma," Molecular Therapy, 22(1):S284, Abstract 734 (2014).

Thomas et al., "An Optimized GD2-Targeting Retroviral Cassette for More Potent and Safer Cellular Therapy of Neuroblastoma and Other Cancers", PLOS ONE, 11(3)E0152196, 19 pages (2016).

Grada et al., "Targeting Lung Cancer using GD2-specific T cells", Abstract No. 833 (p. 43), ASGCT Final Program Addendum, American Society of Gene & Cell Therapy, 15th Annual Meeting, May 16-19, 2012.

* cited by examiner

F.
METDTLLLWVLLLWVPGSTGQVQLQESGPGLVKPSQTLSITCTVSGFSLASYNIHWVRQPPGKGLEWLGVIWAGGS
TNYNSALMSRLTISKDNSKNQVFLKMSSLTAADTAVYYCAKRSDDYSWFAYWGQGTLVTVSSGGGGSGGGGSGGGG
SENQMTQSPSSLSASVGDRVTMTCRASSSVSSSYLHWYQQKSGKAPKVWIYSTSNLASGVPSRFSGSGSGTDYTLT
ISSLQPEDFATYYCQQYSGYPITFGQGTKVEIKRSDP*...*

G.
METDTLLLWVLLLWVPGSTGQVQLQESGPGLVKPSQTLSITCTVSGFSLASYNIHWVRQPPGKGLEWLGVIWAGGS
TNYNSALMSRLTISKDNSKNQVFLKMSSLTAADTAVYYCAKRSDDYSWFAYWGQGTLVTVSSGGGGSGGGGSGGGG
SENQMTQSPSSLSASVGDRVTMTCRASSSVSSSYLHWYQQKSGKAPKVWIYSTSNLASGVPSRFSGSGSGTDYTLT
ISSLQPEDFATYYCQQYSGYPITFGQGTKVEIKRSDP

H.
METDTLLLWVLLLWVPGSTGQVQLQESGPGLVKPSQTLSITCTVSGFSLASYNIHWVRQPPGKGLEWLGVIWAGGS
TNYNSALMSRLTISKDNSKNQVFLKMSSLTAADTAVYYCAKRSDDYSWFAYWGQGTLVTVSSGGGGSGGGGSGGGG
SENQMTQSPSSLSASVGDRVTMTCRASSSVSSSYLHWYQQKSGKAPKVWIYSTSNLASGVPSRFSGSGSGTDYTLT
ISSLQPEDFATYYCQQYSGYPITFGQGTKVEIKR*SDP*

I.
METDTLLLWVLLLWVPGSTGQVQLQESGPGLVKP
SQTLSITCTVSGFSLASYNIHWVRQPPGKGLEWLGVIWAGGSTNYNSALMSRLTISKDNSKNQVFLKMSSLTAADT
AVYYCAKRSDDYSWFAYWGQGTLVTVSSGGGGSGGGGSGGGGSENQMTQSPSSLSASVGDRVTMTCRASSSVSSSY
LHWYQQKSGKAPKVWIYSTSNLASGVPSRFSGSGSGTDYTLTISSLQPEDFATYYCQQYSGYPITFGQGTKVEIKR
SDP *FWVLVVVGGVLACYSLLVTVAFIIFWV*

J.
METDTLLLWVLLLWVPGSTGQVQLQESGPGLVKPSQTLSITCTVSGFSLAS
YNIHWVRQPPGKGLEWLGVIWAGGSTNYNSALMSRLTISKDNSKNQVFLKMSSLTAADTAVYYCAKRSDDYSWFAY
WGQGTLVTVSSGGGGSGGGGSGGGGSENQMTQSPSSLSASVGDRVTMTCRASSSVSSSYLHWYQQKSGKAPKVWIY
STSNLASGVPSRFSGSGSGTDYTLTISSLQPEDFATYYCQQYSGYPITFGQGTKVEIKRSDP *FWVLVV
VGGVLACYSLLVTVAFIIFWV*

FIGURE 12 contd.

| Region | Description |
|---|---|
| | Either iCasp9 or RQR8 |
| | Foot-and-mouth disease 2A peptide |
| Signal | Signal peptide |
| scFv1 | scFv (either muKM666 or huKM666) |
| SDP | Linker and chain break |
| | CD8alpha stalk |
| CD28 TM | CD28 transmembrane domain |
| CD28 endo | CD28 endodomain |
| OX40 endo | OX40 endodomain |
| | CD3 Zeta endodomain |

CHIMERIC ANTIGEN RECEPTOR

FIELD OF THE INVENTION

The present invention relates to chimeric antigen receptor (CAR) which binds the cancer antigen disialoganglioside (GD2). T cells expressing such a CAR are useful in the treatment of cancerous diseases such as neuroblastoma.

BACKGROUND TO THE INVENTION

Disialoganglioside (GD2, pubchem: 6450346) is a sialic acid-containing glycosphingolipid expressed primarily on the cell surface. The function of this carbohydrate antigen is not completely understood; however, it is thought to play an important role in the attachment of tumour cells to extracellular matrix proteins. GD2 is densely, homogenously and almost universally expressed on neuroblastoma. In normal tissues, GD2 expression is largely limited to skin melanocytes, and peripheral pain fibre myelin sheaths. Within the CNS, GD2 appears to be an embryonic antigen but is found dimly expressed in scattered oligodendrocytes and within the posterior pituitary. This makes GD2 well suited for targeted antitumour therapy.

Anti-GD2 antibodies have been extensively tested as therapy in neuroblastoma. Two clones and their derivatives are in current clinical use: clone 3F814 and 3F8. Another clone 14.187 has been tested as a mouse IgG3, after isotype switching to IgG2a (14g2a) and finally after chimerization with human IgG1 to form ch14.18. This latter antibody has resulted in clear efficacy in a randomized study: the US Children's Oncology Group reported a randomised phase III study of ch14:18 in children with high-risk neuroblastoma who had achieved radiological remission after initial treatment. In these patients, there was a 20% improvement in EFS in the ch14:18 arm with a mean follow-up of 2.1 years. Importantly, neurotoxicity most commonly as a chronic pain inducing neuropathy and less commonly an ophthalmoplegia is the main dose-limiting toxicity with these agents.

These therapeutic mAbs continue to be refined: an IL-2 immunocytokine derived from ch14.18 has been described. This is quite a toxic agent with some effect on minimal residual disease, but none against bulky disease. Ch14.18 has been fully humanized and its Fc mutated to inhibit complement activation. This humanized version of Ch14.18 is in clinical study but only very limited data are available. Humanization of the 3F8 antibody has also been described. While clinical data from GD2 serotherapy is encouraging, sustained complete remissions are still limited and there is no evidence for a clinically useful role for antibodies except in the minimal disease setting.

There is thus a need for improved therapeutic approaches to treat neuroblastoma and other GD2-expressing cancers.

Chimeric Antigen Receptors (CARs)

Chimeric antigen receptors are proteins which, in their usual format, graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 1a).

The most common form of these molecules are fusions of single-chain variable fragments (scFv) derived from monoclonal antibodies which recognise a target antigen, fused via a spacer and a transmembrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

Chimeric antigen receptors against GD2 have been described in which the antigen-binding domain is based on the scFv 14g2a (WO 2013/040371 and Yvon et al (2009, Clin Cancer Res 15:5852-5860)).

Human T cells expressing a 14g2a-CD28-OX40ζ-CAR were shown to have some antitumour activity but to be unable to completely eradicate the disease (Yvon et al (2009) as above).

The present inventors sought to make an alternative GD2-targeting CAR with improved properties.

Three different chimeric antigen receptors were compared. The receptors all comprised of the huK666 scFv, the Fc domain of IgG1 mutated to reduce FcR binding and the CD28 transmembrane domain. CAR "28tmZ" has a CD3 Zeta endodomain; "28Z" has a compound CD28-CD3Zeta endodomain; "28OXZ" has a compound endodomain comprising of CD28, OX40 and CD3Zeta, Peripheral blood T-cells from normal donors were transduced with these constructs with retroviral vectors of similar titers. These different T-cell lines were compared, along with non-transduced T-cells as controls. T-cells were challenged with A204 cells (a rhabdomyosarcoma cell line which is GD2 negative), and LAN-1 cells (a neuroblastoma cell line which is GD2 positive). Proliferation and cytokine release show that receptor activity is 28tmZ<28Z<28OXZ.

Figure 8:
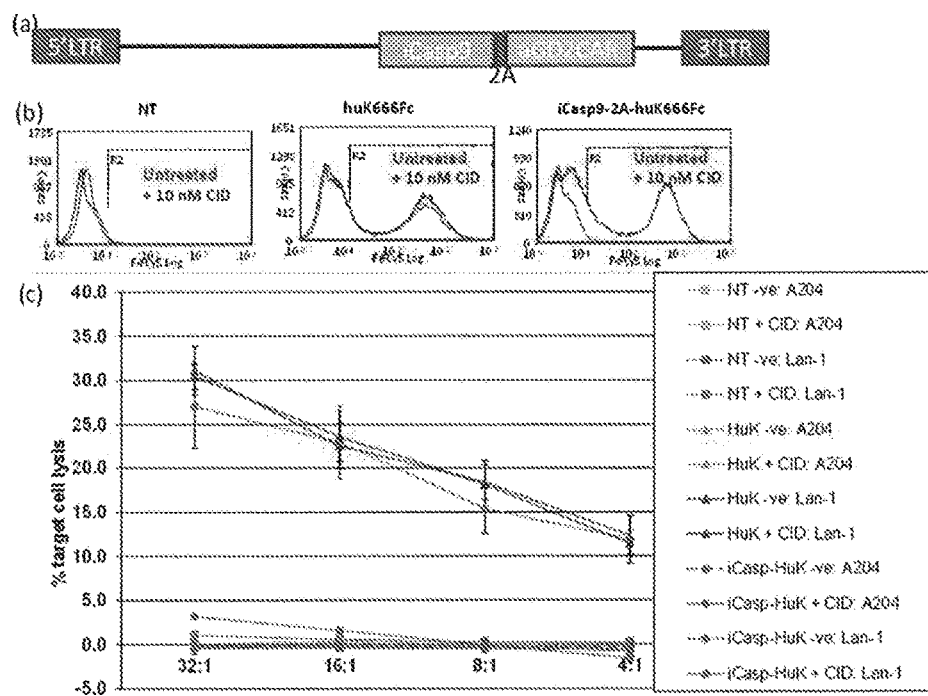

FIG. 8—Co-expression with iCasp9 suicide gene (a) Co-expression of iCasp9 with anti-GD2CAR using FMD-2A sequence; (b) CAR expression in NT T-cells, GD2CAR transduced T-cells and iCasp9-2A-GD2CAR T-cells alone and after treatment with CID; (c) Killing of GD2 positive (LAN-1) and negative (A204) targets with non-transduced, GD2CAR transduced and iCasp9-2A-GD2CAR transduced T-cells with or without treatment with CID. Average of 5 normal donor T-cells.

Figure 9:
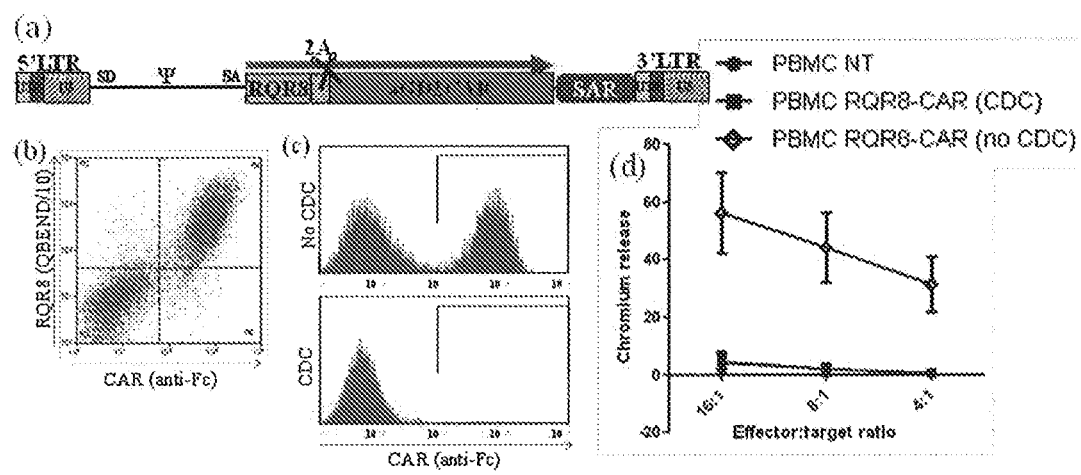

FIG. 9—Co-expression with RQR8 suicide gene (a) CARhuK666Fc was co-expressed with the RQR8 sort-suicide gene in a retroviral vector. (b) T-cells were transduced with this retroviral vector and co-expression of the CAR and RQR8 was determined by staining the transduced T-cells with a polyclonal anti-Fc and the monoclonal antibody QBend10. (c) The CAR positive population from these T-cells could be depleted in the presence of Rituximab and complement. (d) T-cells depleted with Rituximab no longer recognized GD2 expressing targets.

Figure 10:
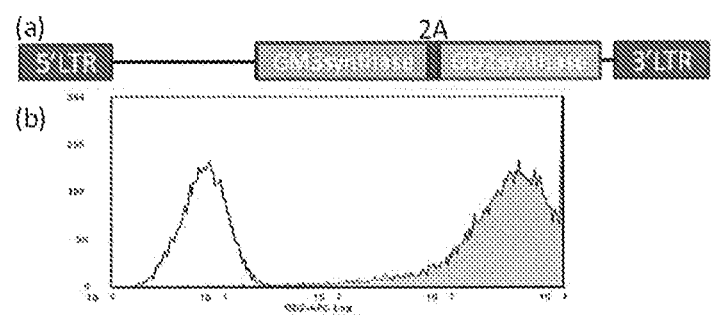

FIG. 10—(a) Bicistronic vector expressing GM3synthase and GD2synthase. (b) SupT1 cells transduced with this vector become GD2 positive (non-transduced empty plot; transduced greyed plot).

Figure 11:
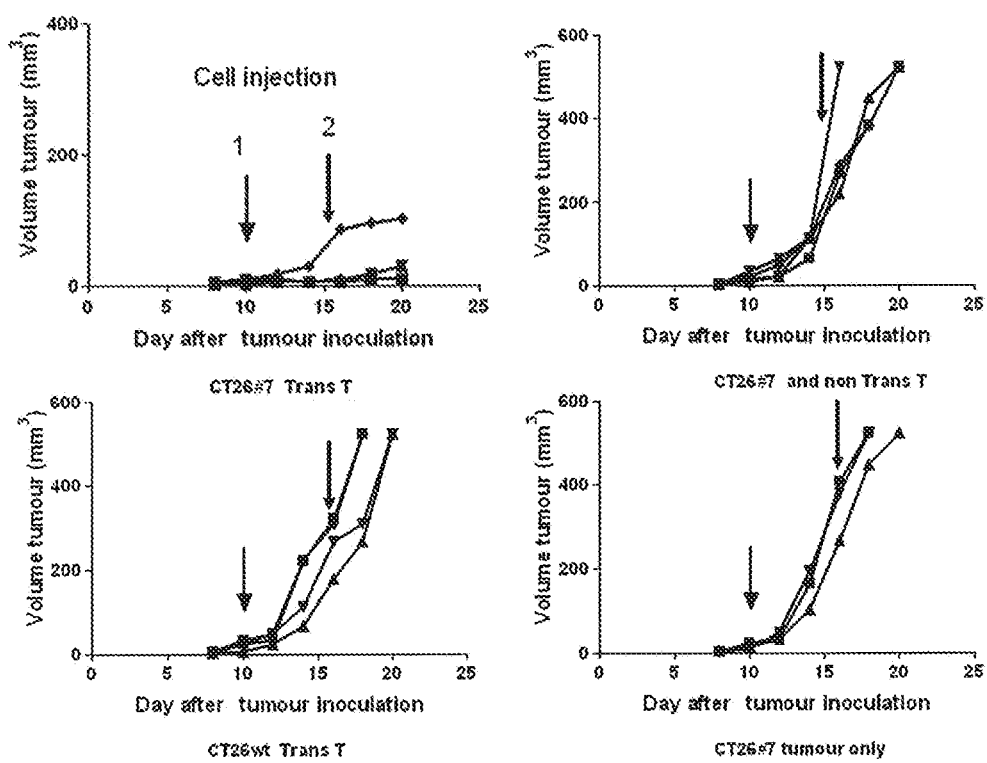
Figure 12:
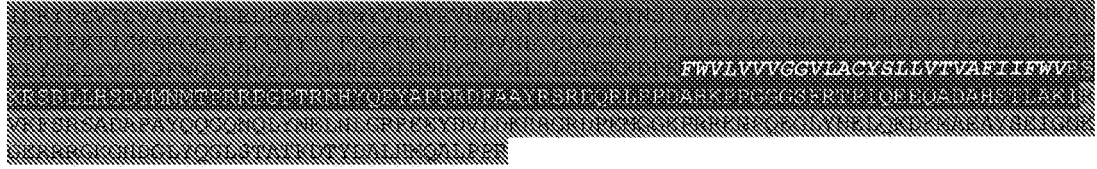
Figure 12:
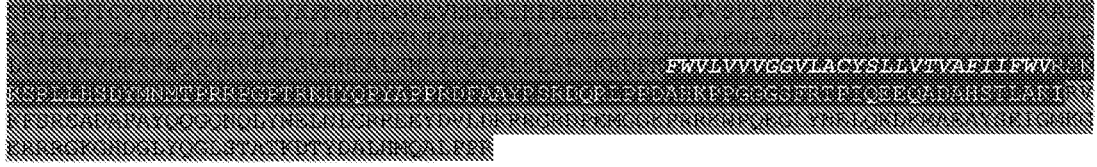
Figure 12:
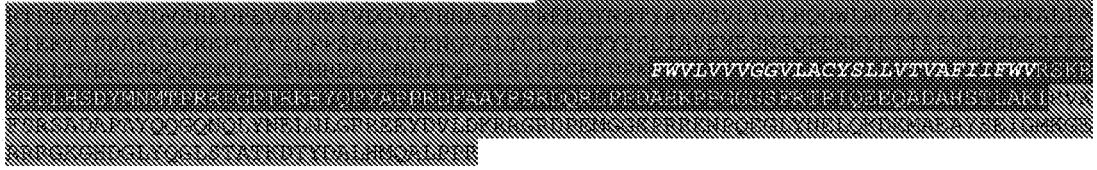
Figure 12:
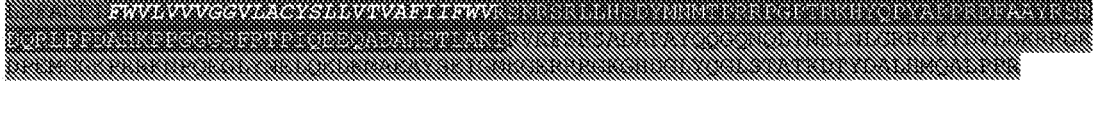
Figure 12:
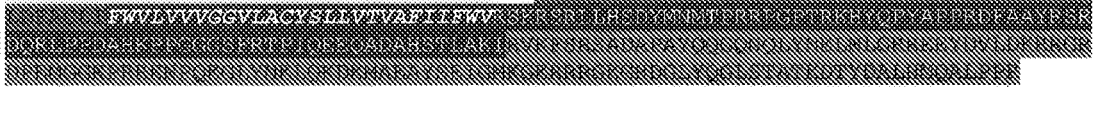

FIG. 11—Growth curves of individual tumours in mice in the following cohorts: top left: mice with GD2 expressing CT26 tumours receiving anti-GD2 CAR splenocytes; top right: GD2 expressing CT26 tumours receiving mock-transduced splenocytes; bottom left: GD2 negative (wt) CT26 tumours with anti-GD2 CAR splenocytes; bottom right: and GD2 expressing CT26 tumours receiving no splenocytes FIG. 12—Amino Acid Sequences A. anti-GD2 CAR shown as (a) in FIG. 2 (muKM666-HCH2CH3-CD28OXZ—SEQ ID No. 26)

Figure 1:
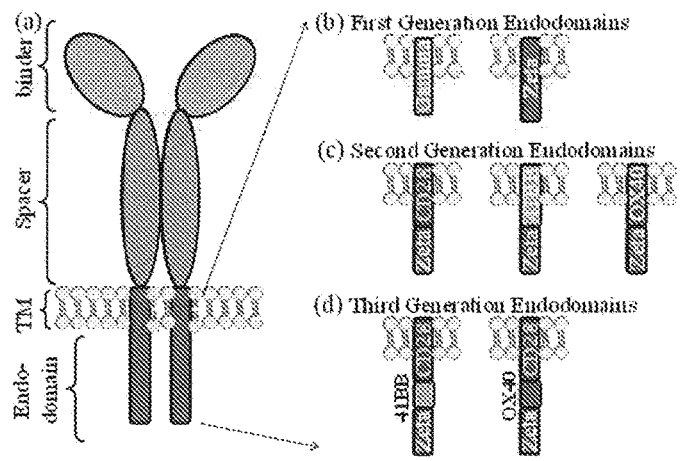
FIG. 1 Chimeric Antigen Receptor (CAR) design. (a) generalized architecture of a CAR: A binding domain recognizes antigen; the spacer elevates the binding domain from the cell surface; the trans-membrane domain anchors the protein to the membrane and the endodomain transmits signals. (b) to (d): Different generations and permutations of CAR endodomains: (b) initial designs transmitted ITAM signals alone through FcεR1-y or CD3-Zeta endodomain, while later designs transmitted additional (c) one or (d) two co-stimulatory signals in cis.
Figure 2:
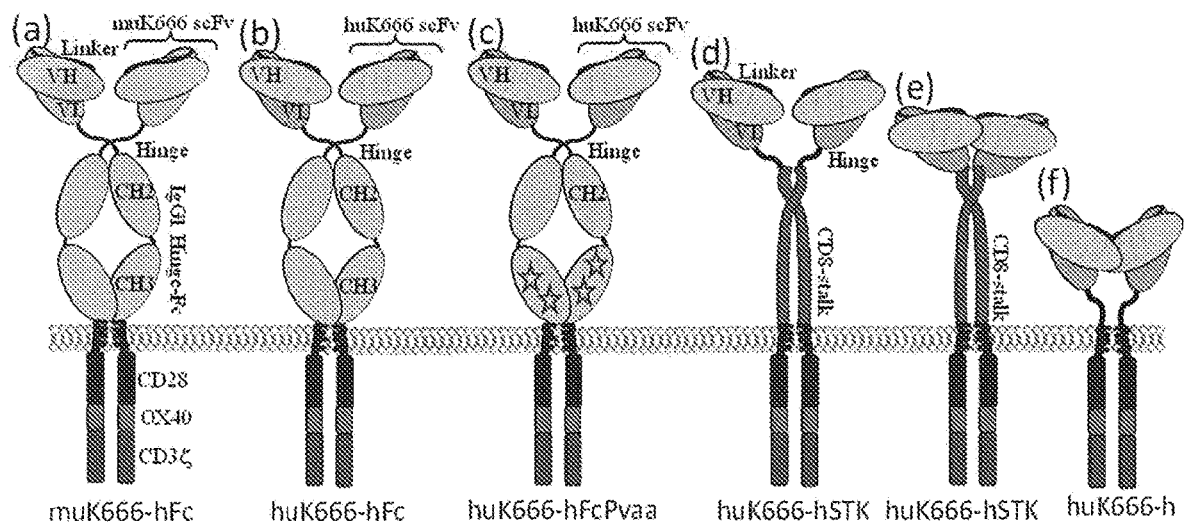
FIG. 2—Variants of anti-GD2 CARs constructed (a) anti-GD2 CAR using mouse KM666 antibody as scFv with human IgG1 spacer and CD28-OX40-Zeta endodomain; (b) anti-GD2 CAR using Nakamura humanized antibody huKM666 in the same format as (a); (c) same format as (b) except Fc domain is modified to remove Fc Receptor recognition motifs; (d) same format as (c) except spacer is IgG1 hinge—CD8 stalk; (e) same as (c) except spacer is CD8 stalk only; (f) same as (c) except spacer is IgG1 hinge only.

B. anti-GD2 CAR shown as (b) in FIG. 2 (huKM666-HCH2CH3-CD28OXZ—SEQ ID No. 27)

C. anti-GD2 CAR shown as (c) in FIG. 2 (huKM666-HCH2CH3pvaa-CD28OXZ—SEQ ID No. 28)

D. anti-GD2 CAR shown as (d) in FIG. 2 (huKM666-HSTK-CD28OXZ—SEQ ID No. 29)

E. anti-GD2 CAR shown as (e) in FIG. 2 (huKM666-STK-CD28XOXZ—SEQ ID No. 30)

F. anti-GD2 CAR shown as (f) in FIG. 2 (huKM666-HNG-CD28OXZ—SEQ ID No.

G. anti-GD2 CAR as shown in (c) FIG. 2 but with 1st generation endodomain (huKM666-HCH2CH3pvaa-CD28tmZ—SEQ ID No. 32)

H. anti-GD2 CAR as shown in (c) FIG. 2 but with 2nd generation endodomain (huMK666-HCH2CH3pvaa-CD28Z—SEQ ID No. 33)

I. anti-GD2 CAR co-expressed with iCasp9 suicide gene—SEQ ID No. 34

J. anti-GD2 CAR co-expressed with RQR8 suicide gene—SEQ ID No. 35

Figure 13:
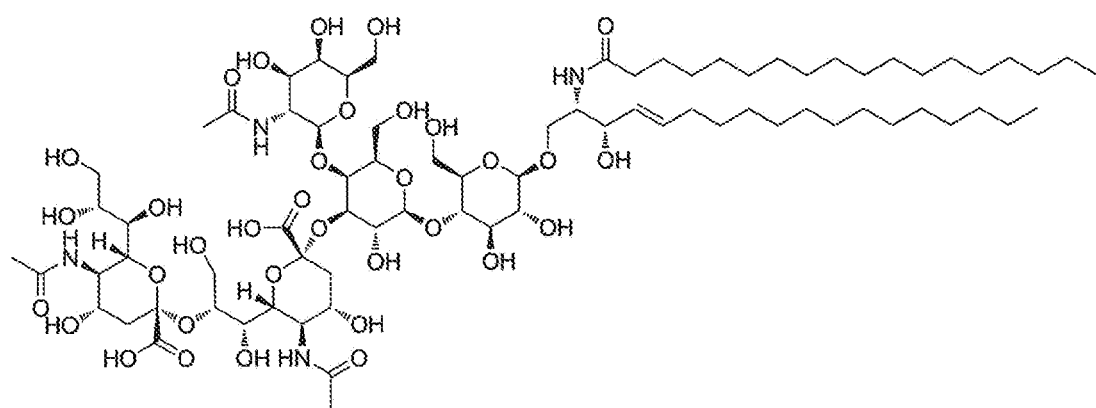

FIG. 13—Structure of GD2

Figure 14:
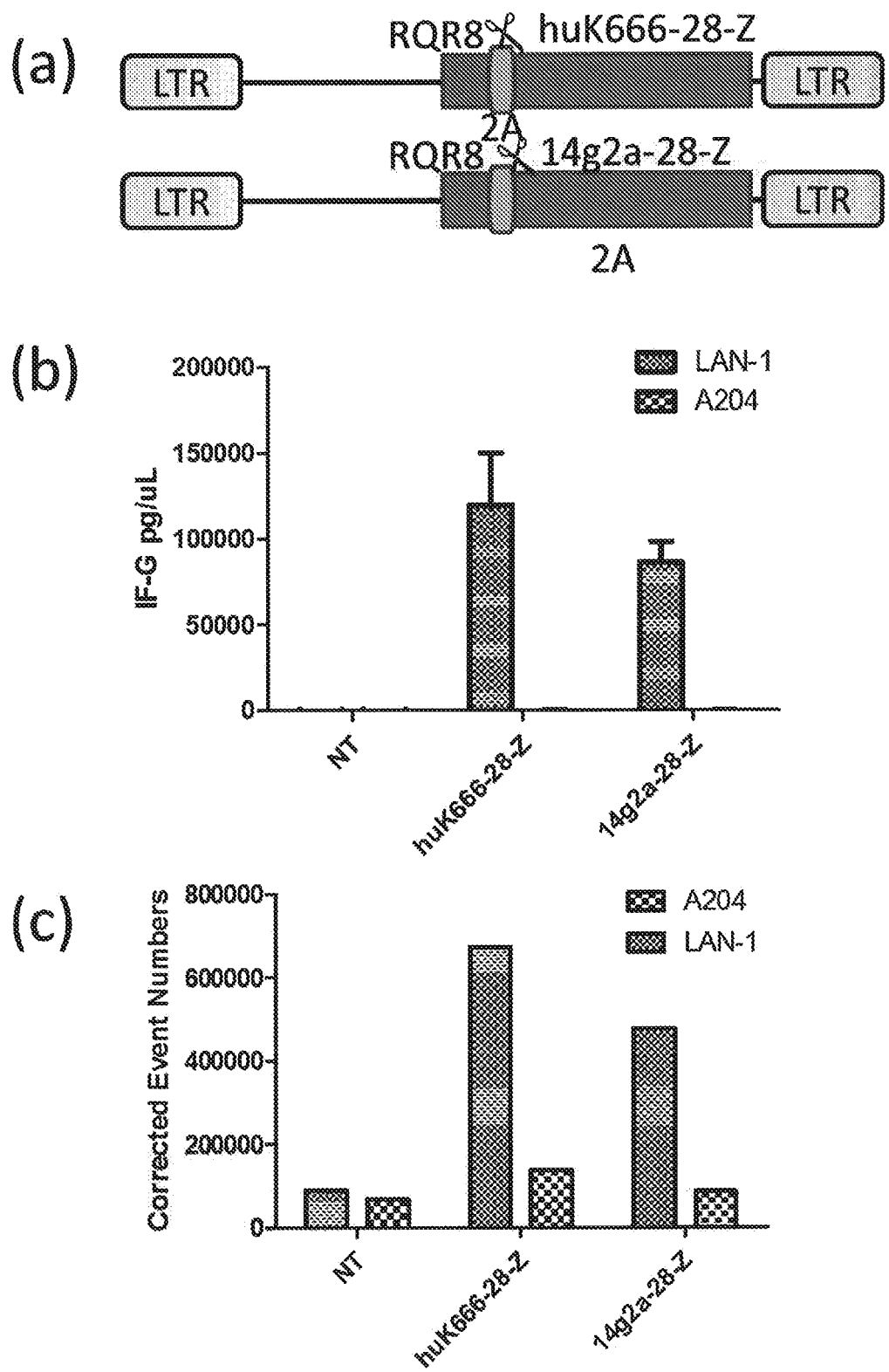

FIG. 14—Comparison of huK666 and 14g2a CARs. (a) maps of constructs tested: Two constructs were tested in primary T-cells. Both are retroviral vectors coding for RQR8 and a 2nd generation GD2 CAR co-expressed with a FMD-2A like sequence. The only difference between constructs is that in one, the scFv is huK666 and in the other it is 14g2a. T-cells transduced with these constructs were challenged 1:1 with either A204 (a GD2 negative rhabdomyosarcoma cell line), and LAN-1 (a GD2 positive cell line). (b) At 24 hours, Interferon-gamma was measured from supernatant. huK666 CAR T-cells produce more IF-G. (c) After one week T-cells are counted, huK666 show more proliferation.

Figure 15:
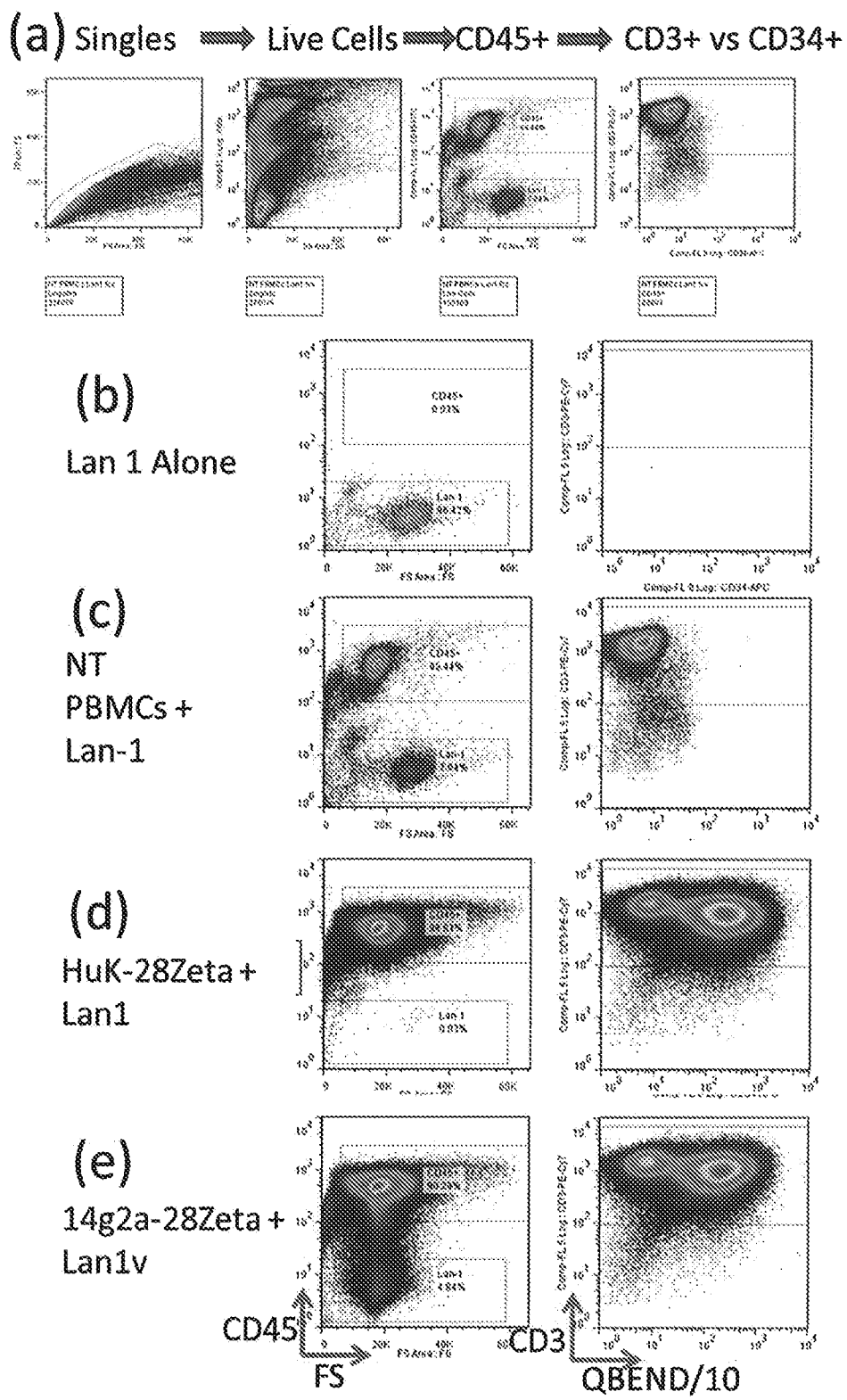

FIG. 15—Flow cytometric analysis of co-culture between huK666 or 14g2a based 2nd generation CARs and Neuroblastoma cell line LAN1. (a) Set up of the experiment. After one week co-culture, cells were harvested and analyzed by flow-cytometry. CD45 expression allowed discrimination from lymphoid cells and non-lymphoid cells with CD45- cells being LAN-1 cells. Further staining with CD3/QBEND/10 allowed counting of CAR T-cells. (b) T-cells alone; (c) NT T-cells and LAN-1 cells; (d) huK666-28-Z CAR T-cells and LAN-1 cells; (e) 14g2a-28-Z CAR T-cells and LAN-1 cells. A residuum of LAN-1 cells is seen in the 14g2a CAR T-cell co-culture.

SUMMARY OF ASPECTS OF THE INVENTION

The present inventors have constructed a new chimeric antigen receptor (CAR) targeting GD2 which comprises a GD2-binding domain based on the K666 antibody.

The anti-GD2 antibody 14g2a can be seen as the gold standard because it is used as a therapeutic antibody and is the only scFv tested to date in a CAR study (PMID: 18978797). The present inventors compared 14g2a and huK666 based CAR in a second generation format as this is the most widely used CAR format used in clinical studies. We found that huK666 CAR T-cells release more IFN-γ, proliferate better and kill more completely than 14g2a equivalents.

Thus, in a first aspect the present invention provides a chimeric antigen receptor (CAR) comprising a disialoganglioside (GD2)-binding domain which comprises a) a heavy chain variable region (VH) having complementarity determining regions (CDRs) with the following sequences:

```
CDR1-
                                             (SEQ ID No. 1)
SYNIH;
```

```
-continued
CDR2-
                                      (SEQ ID No. 2)
VIWAGGSTNYNSALMS CDR3-
                                      (SEQ ID No. 3)
RSDDYSWFAY;
``` and b) a light chain variable region (VL) having CDRs with the following sequences:

```
CDR1-
                                      (SEQ ID No. 4)
RASSSVSSSYLH;

CDR2-
                                      (SEQ ID No. 5)
STSNLAS

CDR3-
                                      (SEQ ID No. 6)
QQYSGYPIT.
```

The GD2 binding domain may comprise a VH domain having the sequence shown as SEQ ID No. 9, or SEQ ID NO 10; or a VL domain having the sequence shown as SEQ ID No 11, or SEQ ID No. 12 or a variant thereof having at least 90% sequence identity which retains the capacity to i) bind GD2 and ii) induce T cell signalling.

The GD2 binding domain may comprise the sequence shown as SEQ ID No 7 or SEQ ID No. 8 or a variant thereof having at least 90% sequence identity which retains the capacity to i) bind GD2 and ii) induce T cell signalling.

The transmembrane domain may comprise the sequence shown as SEQ ID No. 13 or a variant thereof having at least 90% sequence identity which retains the capacity to i) bind GD2 and ii) induce T cell signalling.

The GD2-binding domain and the transmembrane domain may be connected by a spacer.

The spacer may comprise one of the following: a human an IgG1 Fc domain; an IgG1 hinge; an IgG1 hinge-CD8 stalk; or a CD8 stalk.

The spacer may comprise an IgG1 hinge-CD8 stalk or a CD8 stalk.

The spacer may comprise an IgG1 Fc domain or a variant thereof.

The spacer may comprise an IgG1 Fc domain which comprises the sequence shown as SEQ ID No. 23 or SEQ ID No. 24 or a variant thereof having at least 80% sequence identity.

The CAR may comprise or associate with an intracellular T cell signalling domain.

The intracellular T cell signalling domain may comprise one or more of the following endodomains: CD28 endodomain; OX40 and CD3-Zeta endodomain.

The intracellular T cell signalling domain may comprise all of the following endodomains: CD28 endodomain; OX40 and CD3-Zeta endodomain.

The CAR may comprise the sequence shown as any of SEQ ID No. 26 to 35 or a variant thereof which has at least 80% sequence identity but retains the capacity to i) bind GD2 and ii) induce T cell signalling.

In a second aspect, the present invention provides a nucleic acid sequence which encodes a CAR according to the first aspect of the invention.

The nucleic acid sequence may be codon-optimised.

The nucleic acid sequence may comprise the sequence shown as SEQ ID No 25 or a variant thereof having at least 90% sequence identity.

The nucleic acid may also encode a suicide gene.

In a third aspect, the present invention provides a vector which comprises a nucleic acid sequence according to the second aspect of the invention.

In a fourth aspect, the present invention provides a cell which expresses a CAR according to the first aspect of the invention. The cell may be a cytolytic immune cell, such as a T cell or natural killer (NK) cell.

The cell may co-express a CAR according to the first aspect of the invention and a suicide gene.

The suicide gene may, for example, be iCasp9 or RQR8.

In a fifth aspect, the present invention provides a method for making a cell according to the fourth aspect of the invention, which comprises the step of introducing a nucleic acid according to the second aspect of the invention into a cell.

In a sixth aspect, the present invention provides a pharmaceutical composition which comprises a vector according to the third aspect of the invention or a cell according to the second aspect of the invention, together with a pharmaceutically acceptable carrier, diluent or excipient.

In a seventh aspect, the present invention provides a method for treating cancer which comprises the step of administering a vector according to the third aspect of the invention or a cell according to the fourth aspect of the invention to a subject.

The cancer may be neuroblastoma.

In an eighth aspect, the present invention provides a vector according to the third aspect of the invention or a cell according to the fourth aspect of the invention for use in treating a cancer.

In a ninth aspect, the present invention provides the use of according to the third aspect of the invention or a cell according to the fourth aspect of the invention in the manufacture of a medicament for treating cancer.

In a tenth aspect, the present invention provides a method for making a GD2-expressing cell which comprises the step of introducing a nucleic acid encoding GM3 synthase and a nucleic acid encoding GD2 synthase into a cell.

In an eleventh aspect, the present invention provides a GD2-expressing cell which comprises a heterologous nucleic acid encoding GM3 synthase and a heterolgous nucleic acid encoding GD2 synthase.

In an twelfth aspect, the present invention provides method for stimulating a cell according to the fourth aspect of the invention in vitro, which comprises the step of bringing the cell into contact with a GD2-expressing cell according to the eleventh aspect of the invention.

In a thirteenth aspect, the present invention provides an expression cassette expressing a CAR which comprises a scaffold attachment region (SAR).

The expression cassette may express a CAR according to the first aspect of the invention.

DETAILED DESCRIPTION

Chimeric Antigen Receptors (Cars)

Chimeric antigen receptors (CARs), also known as chimeric T cell receptors, artificial T cell receptors and chimeric immunoreceptors, are engineered receptors, which graft an arbitrary specificity onto an immune effector cell. In a classical CAR, the specificity of a monoclonal antibody is grafted on to a T cell. CAR-encoding nucleic acids may be transferred to T cells using, for example, retroviral vectors. In this way, a large number of cancer-specific T cells can be generated for adoptive cell transfer. Phase I clinical studies of this approach show efficacy.

The target-antigen binding domain of a CAR is commonly fused via a spacer and transmembrane domain to a signaling endodomain. When the CAR binds the target-antigen, this results in the transmission of an activating signal to the T-cell it is expressed on.

The CAR of the present invention comprises a GD2 binding domain which is based on the KM666 monoclonal antibody (Nakamura et al (2001) Cancer Immunol. Immunother. 50:275-284).

The CAR of the present invention comprises a GD2-binding domain which comprises a) a heavy chain variable region (VH) having complementarity determining regions (CDRs) with the following sequences:

```
CDR1-
                                      (SEQ ID No. 1)
SYNIH;

CDR2-
                                      (SEQ ID No. 2)
VIWAGGSTNYNSALMS

CDR3-
                                      (SEQ ID No. 3)
RSDDYSWFAY;
``` and b) a light chain variable region (VL) having CDRs with the following sequences:

```
CDR1-
                                      (SEQ ID No. 4)
RASSSVSSSYLH;

CDR2-
                                      (SEQ ID No. 5)
STSNLAS

CDR3-
                                      (SEQ ID No. 6)
QQYSGYPIT.
```

It may be possible to introduce one or more mutations (substitutions, additions or deletions) into the or each CDR without negatively affecting GD2-binding activity. Each CDR may, for example, have one, two or three amino acid mutations.

The CAR of the present invention may comprise one of the following amino acid sequences:

```
(Murine KM666 sequence)
                                      SEQ ID No. 7
QVQLKESGPVLVAPSQTLSITCTVSGFSLASYNIHWVRQPPGKGLEWLGV

IWAGGSTNYNSALMSRLSISKDNSKSQVFLQMNSLQTDDTAMYYCAKRSD

DYSWFAYWGQGTLVTVSASGGGGSGGGGSGGGGSENVLTQSPAIMSASPG

EKVTMTCRASSSVSSSYLHWYQQKSGASPKVWIYSTSNLASGVPGRFSGS

GSGTSYSLTISSVEAEDAATYYCQQYSGYPITFGAGTKVEVKR
```

```
(Humanised KM666 sequence)
                                      SEQ ID No. 8
QVQLQESGPGLVKPSQTLSITCTVSGFSLASYNIHWVRQPPGKGLEWLGV

IWAGGSTNYNSALMSRLTISKDNSKNQVFLKMSSLTAADTAVYYCAKRSD

DYSWFAYWGQGTLVTVSSGGGGSGGGGSGGGGSENQMTQSPSSLSASVGD

RVTMTCRASSSVSSSYLHWYQQKSGKAPKVWIYSTSNLASGVPSRFSGSG

SGTDYTLTISSLQPEDFATYYCQQYSGYPITFGQGTKVEIKR
```

The CAR of the present invention may comprise one of the following VH sequences:

```
(Murine KM666 VH sequence)
                                      SEQ ID No. 9
QVQLKESGPVLVAPSQTLSITCTVSGFSLASYNIHWVRQPPGKGLEWLG
VIWAGGSTNYNSALMSRLSISKDNSKSQVFLQMNSLQTDDTAMYYCAKR
SDDYSWFAYWGQGTLVTVSA
```

```
(Humanised KM666 VH sequence)
                                      SEQ ID No. 10
QVQLQESGPGLVKPSQTLSITCTVSGFSLASYNIHWVRQPPGKGLEWLG
VIWAGGSTNYNSALMSRLTISKDNSKNQVFLKMSSLTAADTAVYYCAKR
SDDYSWFAYWGQGTLVTVSS
```

The CAR of the present invention may comprise one of the following VL sequences:

```
(Murine KM666 VL sequence)
                                      SEQ ID No. 11
ENVLTQSPAIMSASPGEKVTMTCRASSSVSSSYLHWYQQKSGASPKVW
IYSTSNLASGVPGRFSGSGSGTSYSLTISSVEAEDAATYYCQQYSGYP
ITFGAGTKVEVK
```

```
(Humanised KM666 VH sequence)
                                      SEQ ID No. 12
ENQMTQSPSSLSASVGDRVTMTCRASSSVSSSYLHWYQQKSGKAPKVW
IYSTSNLASGVPSRFSGSGSGTDYTLTISSLQPEDFATYYCQQYSGYP
ITFGQGTKVEIK
```

The CAR of the invention may comprise a variant of the sequence shown as SEQ ID No. 7, 8, 9, 10, 11 or 12 having at least 80, 85, 90, 95, 98 or 99% sequence identity, provided that the variant sequence retain the capacity to bind GD2 (when in conjunction with a complementary VL or VH domain, if appropriate).

The percentage identity between two polypeptide sequences may be readily determined by programs such as BLAST which is freely available at blast.ncbi.nlm.nih.gov.

Transmembrane Domain

The CAR of the invention may also comprise a transmembrane domain which spans the membrane. It may comprise a hydrophobic alpha helix. The transmembrane domain may be derived from CD28, which gives good receptor stability.

The transmembrane domain may comprise the sequence shown as SEQ ID No. 13.

```
                                      SEQ ID No. 13
FWVLVVVGGVLACYSLLVTVAFIIFWV
INTRACELLULAR T CELL SIGNALING DOMAIN (ENDODOMAIN)
```

The endodomain is the signal-transmission portion of the CAR. After antigen recognition, receptors cluster and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together.

The endodomain of the CAR of the present invention may comprise the CD28 endodomain and OX40 and CD3-Zeta endodomain.

The transmembrane and intracellular T-cell signalling domain (endodomain) of the CAR of the present invention may comprise the sequence shown as SEQ ID No. 14, 15, 16, 17 or 18 or a variant thereof having at least 80% sequence identity.

```
(CD28 endodomain)
                                          SEQ ID No. 14
RSKRSRLLHSDYMNMTPRRPGPTRKHYQPYAPPRDFAAY (CD40 endodomain)
                                          SEQ ID No. 15
RSRDQRLPPDAHKPPGGGSFRTPIQEEQADAHSTLAKI (CD3 zeta endodomain)
                                          SEQ ID No. 16
RSRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATK
DTYDALHMQALPPR (CD28Z)
                                          SEQ ID No. 17
RSKRSRLLHSDYMNMTPRRPGPTRKHYQPYAPPRDFAAYRSRVKFSRSAD

APAYQQGQNQLYNELNLGRREEYDVLDKRRGRDPEMGGKPRRKNPQEGLY

NELQKDKMAEAYSEIGMKGERRRGKGHDGLYQGLSTATKDTYDALHMQAL

PPR (CD28OXZ)
                                          SEQ ID No. 18
RSKRSRLLHSDYMNMTPRRPGPTRKHYQPYAPPRDFAAYRSRDQRLPPDA

HKPPGGGSFRTPIQEEQADAHSTLAKIRVKFSRSADAPAYQQGQNQLYNE

LNLGRREEYDVLDKRRGRDPEMGGKPRRKNPQEGLYNELQKDKMAEAYSE

IGMKGERRRGKGHDGLYQGLSTATKDTYDALHMQALPPR
```

A variant sequence may have at least 80%, 85%, 90%, 95%, 98% or 99% sequence identity to SEQ ID No. 13, 14, 15, 16, 17 or 18, provided that the sequence provides an effective transmembrane domain/intracellular T cell signaling domain.

Signal Peptide

The CAR of the present invention may comprise a signal peptide so that when the CAR is expressed inside a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The CAR of the invention may have the general formula:
Signal peptide—GD2-binding domain—spacer domain—transmembrane domain—intracellular T cell signaling domain.

The signal peptide may comprise the SEQ ID No. 19 or a variant thereof having 5, 4, 3, 2 or 1 amino acid mutations (insertions, substitutions or additions) provided that the signal peptide still functions to cause cell surface expression of the CAR.

```
SEQ ID No. 19:
METDTLLLWVLLLWVPGSTG
```

The signal peptide of SEQ ID No. 19 is compact and highly efficient. It is predicted to give about 95% cleavage after the terminal glycine, giving efficient removal by signal peptidase.

Spacer

The CAR of the present invention may comprise a spacer sequence to connect the GD2-binding domain with the transmembrane domain and spatially separate the GD2-binding domain from the endodomain. A flexible spacer allows to the GD2-binding domain to orient in different directions to enable GD2 binding.

The spacer sequence may, for example, comprise an IgG1 Fc region, an IgG1 hinge or a CD8 stalk, or a combination thereof. The spacer may alternatively comprise an alternative sequence which has similar length and/or domain spacing properties as an IgG1 Fc region, an IgG1 hinge or a CD8 stalk.

A human IgG1 spacer may be altered to remove Fc binding motifs.

Examples of amino acid sequences for these spacers are given below:

```
(hinge-CH2CH3 of human IgG1)
                                          SEQ ID No. 2
AEPKSPDKTHTCPPCPAPPVAGPSVFLFPPKPKDTLMIARTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGKKD (human CD8 stalk):
                                          SEQ ID No. 21
TTTPAPRPPTPAPTIASQPLSLRPEACRPAAGGAVHTRGLDFACDI (human IgG1 hinge):
                                          SEQ ID No. 22
AEPKSPDKTHTCPPCPKDPK (IgG1 Hinge-Fc)
                                          SEQ ID No. 23
AEPKSPDKTHTCPPCPAPELLGGPSVFLFPPKPKDILMISRTPEVTCVV

VDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKN

QVSLICLVKGFYPSDIAVEWESNGQPENNYKTTPPVLDSDGSFFLYSKL

TVDKSRWQQGNVFSCSVMHEALHNHYTQKSLSLSPGKKDPK (IgG1 Hinge-Fc modified to remove Fc receptor
recognition motifs)
                                          SEQ ID No. 24
AEPKSPDKTHTCPPCPAPPVA*GPSVFLFPPKPKDTLMIARTPEVTCVV

VDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKN
```

-continued

QVSLTCLVKGFYPSDIAVEWESNGQPENNYKTTPPVLDSDGSFFLYSKL

TVDKSRWQQGNVFSCSVMHEALHNHYTQKSLSLSPGKKDPK

Modified residues are underlined; * denotes a deletion.

GD2

GD2 is a disialoganglioside expressed on tumours of neuroectodermal origin, including human neuroblastoma and melanoma, with highly restricted expression on normal tissues, principally to the cerebellum and peripheral nerves in humans.

The relatively tumour specific expression of GD2 makes it a suitable target for immunotherapy.

Nucleic Acid Sequence

The second aspect of the invention relates to a nucleic acid sequence which codes for a CAR of the first aspect of the invention.

The nucleic acid sequence may be capable of encoding a CAR having the amino acid sequence shown as any of SEQ ID No. 26-35.

The nucleic acid sequence may be or comprise the following sequence:

```
DNA sequence of retroviral cassette comprising of anti-GD2 CAR co-expressed with
RQR8    suicide gene with a codon-optimized frame and a SAR region to enhance expression
                                                                    SEQ ID No. 25
   1    tgaaagaccc cacctgtagg tttggcaagc tagcttaagt aacgccattt tgcaaggcat ggaaaaatac
        >>.........................LTR...............................>

71    ataactgaga atagaaaagt tcagatcaag gtcaggaaca gatggaacag ctgaatatgg gccaaacagg
        >..........................LTR...............................>

141    atatctgtgg taagcagttc ctgccccggc tcagggccaa gaacagatgg aacagctgaa tatgggccaa
        >..........................LTR...............................>

211    acaggatatc tgtggtaagc agttcctgcc ccggctcagg gccaagaaca gatggtcccc agatgcggtc
        >..........................LTR...............................>

281    cagccctcag cagtttctag agaaccatca gatgtttcca gggtgcccca aggacctgaa atgaccctgt
        >..........................LTR...............................>

351    gccttatttg aactaaccaa tcagttcgct tctcgcttct gttcgcgcgc ttatgctccc cgagtcaat
        >..........................LTR...............................>

421    aaaagagccc acaaccoctc actcggggcg ccagtcctcc gattgactga gtcgcccggg tacccgtgta
        >..........................LTR...............................>

491    tccaataaac cctcttgcag ttgcatccga cttgtggtct cgctgttcct tgggagggtc tcctctgagt
        >..........................LTR...............................>

561    gattgactac ccgtcagcgg gggtctttca tttggggggct cgtccgggat cgggagaccc ctgcccaggg
        >............LTR.............>>

631    accaccgacc caccaccggg aggtaagctg gccagcaact tatctgtgtc tgtccgattg tctagtgtct 701    atgactgatt ttatgcgcct gcgtcggtac tagttagcta actagctctg tatctggcgg acccgtggtg
                                Eco52I
                                ------
 771    gaactgacga gttcggaaca cccggccgca accctgggag acgtcccagg gacttcgggg gccgttttg
                    PshAI
                    ----------
 841    tggcccgacc tgagtcctaa aatcccgatc gtttaggact ctttggtgca ccccccttag aggagggata 911    tgtggttctg gtaggagacg agaacctaaa acagttcccg cctccgtctg aattttgct tccggttgg 981    gaccgaagcc gcgccgcgcg tcttgtctgc tgcagcatcg ttctgtgttg tctctgtctg actgtgtttc
                                SrfI
                                --------
1051    tgtatttgtc tgaaaatatg ggcccgggct agcctgttac cactccetta agtttgacct taggtcactg 1121    gaaagatgtc gagcggatcg ctcacaacca gtcggtagat gtcaagaaga gacgttgggt taccttctgc 1191    tctgcagaat ggccaacctt taacgtcgga tggccgcgag acggcacctt taaccgagac ctcatcaccc 1261    aggttaagat caaggtcttt tcacctggcc cgcatggaca cccagaccag gtggggtaca tcgtgacctg 1331    ggaagccttg gctttgacc ccctccctg ggtcaagccc tttgtacacc ctaagcctcc gcctcctctt 1401    cctccatccg ccccgtctct ccccttgaa cctcctcgtt cgaccccgcc tcgatcctcc ctttatccag
                                BglII
                                -------
1471    ccctcactcc ttctctaggc gccccatat ggccatatga gatcttatat ggggcaccc cgccccttgt 1541    aaacttccct gaccctgaca tgacaagagt tactaacagc cctctctcc aagctcactt acaggctctc
```

-continued

```
                                                                AgeI
                                                                ------
1611  tacttagtcc agcacgaagt ctggagacct ctggcggcag cctaccaaga acaactggac cgaccggtgg 1681  tacctcaccc ttaccgagtc ggcgacacag tgtgggtccg ccgacaccag actaagaacc tagaacctcg AccI
                                                 -------
1751  ctggaaagga ccttacacag tcctgctgac cacccccacc gccctcaaag tagacggcat cgcagcttgg PmlI
                 ------
1821  atacacgccg cccacgtgaa ggctgccgac cccggggtg gaccatcctc tagactgcca acatgggcac
                                                                               >>.orf.>
                                                                               >>RQR8.>

1891  cagcctgctg tgctggatgg ccctgtgcct gctgggcgcc gaccacgccg atgcctgccc ctacagcaac
      >...................................orf........................................>
      >...................................RQR8.......................................>

1961  cccagcctgt gcagcggagg cggcggcagc gagctgcccc cccagggcac cttctccaac gtgtccacca
      >...................................orf........................................>
      >...................................RQR8.......................................>

2031  acgtgagccc agccaagccc accaccaccg cctgtcctta ttccaatcct tccctgtgta gcggaggggg
      >...................................orf........................................>
      >...................................RQR8.......................................>

2101  aggcagccca gcccccagac ctcccacccc agccccacc atcgccagcc agcctctgag cctgagaccc
      >...................................orf........................................>
      >...................................RQR8.......................................>

SgrAI
                ---------
2171  gaggcctgcc gcccagccgc cggcggcgcc gtgcacacca gaggcctgga tttcgcctgc gatatctaca
      >...................................orf........................................>
      >...................................RQR8.......................................>

BclI
                                                                    -------
2241  tctgggcccc actggccggc acctgtggcg tgctgctgct gagcctggtg atcaccctgt actgcaacca
      >...................................orf........................................>
      >...................................RQR8.......................................>

2311  ccgcaaccgc aggcgcgtgt gcaagtgccc caggcccgtg gtgagagccg agggcagagg cagcctgctg
      >...................................orf........................................>
      >...............RQR8..................>>
                                              >>..........FMD-2A.......>

2381  acctgcggcg acgtggagga gaacccaggc cccatggaga ccgacaccct gctgctgtgg gtgctgctgc
      >...................................orf........................................>
      >...............RQR8.........>>
                              >>..................CAR..................>

2451  tgtgggtgcc aggcagcacc ggccaggtgc agctgcagga gtctggccca ggcctggtga agcccagcca
      >...................................orf........................................>
      >...................................CAR........................................>

2521  gaccctgagc atcacctgca ccgtgagcgg cttcagcctg ccagctaca acatccactg ggtgcggcag
      >...................................orf........................................>
      >...................................CAR........................................>

2591  cccccaggca agggcctgga gtggctgggc gtgatctggg ctggcggcag caccaactac aacagcgccc
      >...................................orf........................................>
      >...................................CAR........................................>

2661  tgatgagccg gctgaccatc agcaaggaca acagcaagaa ccaggtgttc ctgaagatga gcagcctgac
      >...................................orf........................................>
      >...................................CAR........................................>

2731  agccgccgac accgccgtgt actactgcgc caagcggagc gacgactaca gctggttcgc ctactggggc
      >...................................orf........................................>
      >...................................CAR........................................>

2801  cagggcaccc tggtgaccgt gagctctggc ggaggcggct ctggcggagg cggctctggc ggaggcggca
      >...................................orf........................................>
      >...................................CAR........................................>

2871  gcgagaacca gatgacccag agccccagca gcttgagcgc cagcgtgggc gaccgggtga ccatgacctg
      >...................................orf........................................>
      >...................................CAR........................................>
```

```
2941  cagagccagc agcagcgtga gcagcagcta cctgcactgg taccagcaga agagcggcaa ggccccaaag
      >...................................orf........................................>
      >...................................CAR........................................>

3011  gtgtggatct acagcaccag caacctggcc agcggcgtgc ccagccggtt cagcggcagc ggcagcggca
      >...................................orf........................................>
      >...................................CAR........................................>

3081  ccgactacac cctgaccatc agcagcctgc agcccgagga cttcgccacc tactactgcc agcagtacag
      >...................................orf........................................>
      >...................................CAR........................................>

BamHI
                                                                       ------
3151  cggctacccc atcaccttcg gccagggcac caaggtggag atcaagcggt cggatcccgc cgagcccaaa
      >...................................orf........................................>
      >...................................CAR........................................>

FseI
                                                 ---------
3221  tctcctgaca aaactcacac atgcccaccg tgcccagcac ctcccgtggc cggccgtca gtcttcctct
      >...................................orf........................................>
      >...................................CAR........................................>

3291  tccccccaaa acccaaggac accctcatga tcgccggac ccctgaggtc acatgcgtgg tggtggacgt
      >...................................orf........................................>
      >...................................CAR........................................>

3361  gagccacgaa gaccctgagg tcaagttcaa ctggtacgtg gacggcgtgg aggtgcataa tgccaagaca
      >...................................orf........................................>
      >...................................CAR........................................>

SacII
         ------
3431  aagccgcggg aggagcagta caacagcacg taccgtgtgg tcagcgtcct caccgtcctg caccaggact
      >...................................orf........................................>
      >...................................CAR........................................>

3501  ggctgaatgg caaggagtac aagtgcaagg tctccaacaa agccctccca gcccccatcg agaaaaccat
      >...................................orf........................................>
      >...................................CAR........................................>

3571  ctccaaagcc aaagggcagc cccgagaacc acaggtgtac accctgcccc catcccggga tgagctgacc
      >...................................orf........................................>
      >...................................CAR........................................>

3641  aagaaccagg tcagcctgac ctgcctggtc aaaggcttct atcccagcga catcgccgtg gagtgggaga
      >...................................orf........................................>
      >...................................CAR........................................>

3711  gcaatgggca accggagaac aactacaaga ccacgcctcc cgtgctggac tccgacggct ccttcttcct
      >...................................orf........................................>
      >...................................CAR........................................>

Ppu10I
                                                                              ------
                                                                              NsiI
                                                                              ------
                                                                              BfrBI
                                                                              ------
3761  ctacagcaag ctcaccgtgg acaagagcag gtggcagcag gggaacgtct tctcatgctc cgtgatgcat
      >...................................orf........................................>
      >...................................CAR........................................>

Van91I
                                                                           ----------
3851  gaggccctgc acaatcacta tacccagaaa tctctgagtc tgagcccagg caagaaggac cccaagttct
      >...................................orf........................................>
      >...................................CAR........................................>

3921  gggtcctggt ggtggtggga ggcgtgctgg cctgttactc tctcctggtg accgtggcct tcatcatctt
      >...................................orf........................................>
      >...................................CAR........................................>

3991  ctgggtgcgc tccaagagga gcaggctcct gcacagtgac tacatgaaca tgactccccg ccgcccggg
      >...................................orf........................................>
      >...................................CAR........................................>
```

```
                                                              -continued
4061  cccacccgca agcattacca gccctatgcc ccaccacgcg acttcgcagc ctatcgctcc cgggtgaagt
      >....................................orf....................................>
      >....................................CAR....................................>

4131  tctctcgctc tgccgatgcc ccagcctatc agcagggcca gaatcagctg tacaatgaac tgaacctggg
      >....................................orf....................................>
      >....................................CAR....................................>

4201  caggcgggag gagtacgacg tgctggataa gcggagaggc agagaccccg agatgggcgg caaaccacgg
      >....................................orf....................................>
      >....................................CAR....................................>

4271  cgcaaaaatc cccaggaggg actctataac gagctgcaga aggacaaaat ggccgaggcc tattccgaga
      >....................................orf....................................>
      >....................................CAR....................................>

4341  tcggcatgaa gggagagaga agacgcggaa agggccacga cggcctgtat cagggattgt ccaccgctac
      >....................................orf....................................>
      >....................................CAR....................................>

MluI   ClaI
                                                                       -------------
4411  aaaagataca tatgatgccc tgcacatgca ggccctgcca cccagatgac gcgtatcgat actgttctca
      >...................orf.........................>>
      >...................CAR.........................>>
                                                                          >>.SAR..>

4481  tcacatcata tcaaggttat ataccatcaa tattgccaca gatgttactt agccttttaa tatttctcta
      >...................................SAR......................................>

4551  atttagtgta tatgcaatga tagttctctg atttctgaga ttgagtttct catgtgtaat gattatttag
      >...................................SAR......................................>

4621  agtttctctt tcatctgttc aaattttttgt ctagttttat tttttactga tttgtaagac ttcttttat
      >...................................SAR......................................>

4691  aatctgcata ttacaattct ctttactggg gtgttgcaaa tattttctgt cattctatgg cctgactttt
      >...................................SAR......................................>

4761  cttaatggtt ttttaatttt aaaaataagt cttaatattc atgcaatcta attaacaatc ttttctttgt
      >...................................SAR......................................>

SphI
                                                              ------
4831  ggttaggact ttgagtcata agaattttt ctctacactg aagtcatgat ggcatgcttc tatattattt
      >...................................SAR......................................>

4901  tctaaaagat ttaaagtttt gccttctcca tttagactta taattcactg gaattttttt gtgtgtatgg
      >...................................SAR......................................>

4971  tatgacatat gggttcccct ttattttta catataaata tatttccctg tttttctaaa aaagaaaaag
      >...................................SAR......................................>

5041  atcatcattt tcccattgta aaatgccata ttttttttcat aggtcactta catatatcaa tgggtctgtt
      >...................................SAR......................................>

5111  tctgagctct actctatttt atcagcctca ctgtctatcc ccacacatct catgctttgc totaaatott
      >...................................SAR......................................>

5181  gatatttagt ggaacattct ttcccatttt gttctacaag aatattttg ttattgtctt tgggctttct
      >...................................SAR......................................>

5251  atatacattt tgaaatgagg ttgacaagtt cggattagtc caatttgtta aagacaggat atcagtggtc
      >.............SAR...............>>

5321  caggctctag ttttgactca acaatatcac cagctgaagc ctatagagta cgagccatag ataaaataaa 5391  agattttatt tagtctccag aaaaagggg gaatgaaaga ccccacctgt aggtttggca agctagctta
                                          >>..................LTR....................>

5461  agtaacgcca ttttgcaagg catggaaaaa tacataactg agaatagaga agttcagatc aaggtcagga
      >.........................LTR..........................................>

5531  acagatggaa cagctgaata tgggccaaac aggatatctg tggtaagcag ttcctgcccc ggctcagggc
      >.........................LTR..........................................>

5601  caagaacaga tggaacagct gaatatgggc caaacaggat atctgtggta agcagttcct gcccggctc
      >.........................LTR..........................................>

5671  agggccaaga acagatggtc cccagatgcg gtccagccct cagcagtttc tagagaacca tcagatgttt
      >.........................LTR..........................................>
```

```
5741  ccagggtgcc ccaaggacct gaaatgaccc tgtgccttat ttgaactaac caatcagttc gcttctcgct
      >....................................LTR....................................>

5611  tctgttcgcg cgcttctgct ccccgagctc aataaaagag cccacaaccc ctcactcggg gcgccagtcc
      >....................................LTR....................................>

5881  tccgattgac tgagtcgccc gggtacccgt gtatccaata aaccctcttg cagttgcatc cgacttgtgg
      >....................................LTR....................................>

5951  tctcgctgtt ccttgggagg gtctcctctg agtgattgac tacccgtcag cgggggtctt tcac
      >...............................LTR..................................>>
```

The nucleic acid sequence may encode the same amino acid sequence as that encoded by SEQ ID No. 25, but may have a different nucleic acid sequence, due to the degeneracy of the genetic code. The nucleic acid sequence may have at least 80, 85, 90, 95, 98 or 99% identity to the sequence shown as SEQ ID No. 25, provided that it encodes a CAR as defined in the first aspect of the invention.

Suicide Genes

Since T-cells engraft and are autonomous, a means of selectively deleting CAR T-cells in recipients of anti-GD2 CAR T-cells is desirable. Suicide genes are genetically encodable mechanisms which result in selective destruction of infused T-cells in the face of unacceptable toxicity. The earliest clinical experience with suicide genes is with the Herpes Virus Thymidine Kinase (HSV-TK) which renders T-cells susceptible to Ganciclovir. HSV-TK is a highly effective suicide gene. However, pre-formed immune responses may restrict its use to clinical settings of considerable immunosuppression such as haploidentical stem cell transplantation. Inducible Caspase 9 (iCasp9) is a suicide gene constructed by replacing the activating domain of Caspase 9 with a modified FKBP12. iCasp9 is activated by an otherwise inert small molecular chemical inducer of dimerization (CID). iCasp9 has been recently tested in the setting of haploidentical HSCT and can abort GvHD. The biggest limitation of iCasp9 is dependence on availability of clinical grade proprietary CID. Both iCasp9 and HSV-TK are intracellular proteins, so when used as the sole transgene, they have been co-expressed with a marker gene to allow selection of transduced cells.

An iCasp9 may comprise the sequence shown as SEQ ID No. 36 or a variant thereof having at least 80, 90, 95 or 98% sequence identity.

SEQ ID No. 36
MLEGVQVETISPGDGRTFPKRGQTCVVHYTGMLEDGKKVDSSRDRNKPF

KFMLGKQEVIRGWEEGVAQMSVGQRAKLTISPDYAYGATGHPGIIPPHA

TLVFDVELLKLESGGGSGVDGFGDVGALESLRGNADLAYILSMEPCGHC

LIINNVNFCRESGLRTRTGSNIDCEKLRRRFSSLHFMVEVKGDLTAKKM

VLALLELAQQDHGALDCCVVVILSHGCQASHLQFPGAVYGTDGCPVSVE

KIVNIFNGTSCPSLGGKPKLFFIQACGGEQKDHGFEVASTSPEDESPGS

NPEPDATPFQEGLRTFDQLDAISSLPTPSDIFVSYSTFPGFVSWRDPKS

GSWYVETLDDIFEQWAHSEDLQSLLLRVANAVSVKGIYKQMPGCFNFLR

KKLFFKTSAS

The present inventors have recently described a novel marker/suicide gene known as RQR8 which can be detected with the antibody QBEnd10 and expressing cells lysed with the therapeutic antibody Rituximab.

An RQR8 may comprise the sequence shown as SEQ ID No. 37 or a variant thereof having at least 80, 90, 95 or 98% sequence identity.

SEQ ID No. 37
MGTSLLCWMALCLLGADHADACPYSNPSLCSGGGGSELPTQGTFSNVST

NVSPAKPTTTACPYSNPSLCSGGGGSPAPRPPTPAPTIASQPLSLRPEA

CRPAAGGAVHTRGLDFACDIYIWAPLAGTCGVLLLSLVITLYCNHRNRR

RVCKCPRPVV

The suicide gene may be expressed as a single polypeptide with the CAR, for example by using a self-cleaving peptide between the two sequences.

Vector

The present invention also provides a vector which comprises a nucleic acid sequence according to the present invention. Such a vector may be used to introduce the nucleic acid sequence into a host cell so that it expresses and produces a molecule according to the first aspect of the invention.

The vector may, for example, be a plasmid or a viral vector, such as a retroviral vector or a lentiviral vector.

The vector may be capable of transfecting or transducing a T cell.

The vector may also comprise a nucleic acid sequence encoding a suicide gene, such as iCasp9 or RQR8.

Host Cell

The invention also provides a host cell which comprises a nucleic acid according to the invention. The host cell may be capable of expressing a CAR according to the first aspect of the invention.

The host cell may be a cytolytic immune cell such as a human T cell or natural killer (NK) cell.

A T-cell capable of expressing a CAR according to the invention may be made by transducing or transfecting a T cell with CAR-encoding nucleic acid.

The CAR T-cell may be generated ex vivo. The T cell may be from a peripheral blood mononuclear cell (PBMC) sample from the patient or a donor. T cells may be activated and/or expanded prior to being transduced with CAR-encoding nucleic acid, for example by treatment with an anti-CD3 monoclonal antibody.

Pharmaceutical Composition

The present invention also relates to a pharmaceutical composition containing a vector or a CAR-expressing T cell of the invention together with a pharmaceutically acceptable carrier, diluent or excipient, and optionally one or more further pharmaceutically active polypeptides and/or compounds. Such a formulation may, for example, be in a form suitable for intravenous infusion).

Method of Treatment

T cells expressing a CAR molecule of the present invention are capable of killing cancer cells, such as neuroblastoma cells. CAR-expressing T cells may either be created ex vivo either from a patient's own peripheral blood (1$^{st}$ party), or in the setting of a haematopoietic stem cell transplant from donor peripheral blood (2$^{nd}$ party), or peripheral blood from an unconnected donor (3$^{rd}$ party). Alternatively, CAR T-cells may be derived from ex-vivo differentiation of inducible progenitor cells or embryonic progenitor cells to T-cells. In these instances, CAR T-cells are generated by introducing DNA or RNA coding for the CAR by one of many means including transduction with a viral vector, transfection with DNA or RNA.

T cells expressing a CAR molecule of the present invention may be used for the treatment of a cancerous disease, in particular a cancerous disease associated with GD2 expression.

The cancer may be an ectodermal tumour.

Examples of cancers which correlate with elevated GD2 expression levels are: neuroblastoma, melanoma, medulloblastoma, soft-tissue sarcomas, osteosarcoma and small-cell lung cancers such as NSCLC.

A method for the treatment of disease relates to the therapeutic use of a vector or T cell of the invention. In this respect, the vector or T cell may be administered to a subject having an existing disease or condition in order to lessen, reduce or improve at least one symptom associated with the disease and/or to slow down, reduce or block the progression of the disease. The method of the invention may cause or promote T-cell mediated killing of GD2-expressing cells, such as cancer cells.

GD2 Expressing Cell

The invention also provides a method for making a GD2-expressing cell which comprises the step of introducing a nucleic acid encoding GM3 synthase and a nucleic acid encoding GD2 synthase into a cell.

The nucleic acid may be introduced by, for example, transfection or transduction, using a vector such as a plasmid or viral vector.

The invention also relates to a GD2-expressing cell which comprises a heterologous nucleic acid encoding GM3 synthase and a heterologous nucleic acid encoding GD2 synthase.

The nucleic acid may be "heterologous" in the sense that it is not usually present in the cell. It is an artificially introduced recombinant nucleic acid sequence.

The cell may be from a cell line.

The cell may be used for stimulating GD2CAR T-cells in culture, such as the T cells of the present invention.

The invention will now be further described by way of Examples, which are meant to serve to assist one of ordinary skill in the art in carrying out the invention and are not intended in any way to limit the scope of the invention.

EXAMPLES

Example 1

Using the Humanized Antibody huK666 as a Binder

Figure 3:
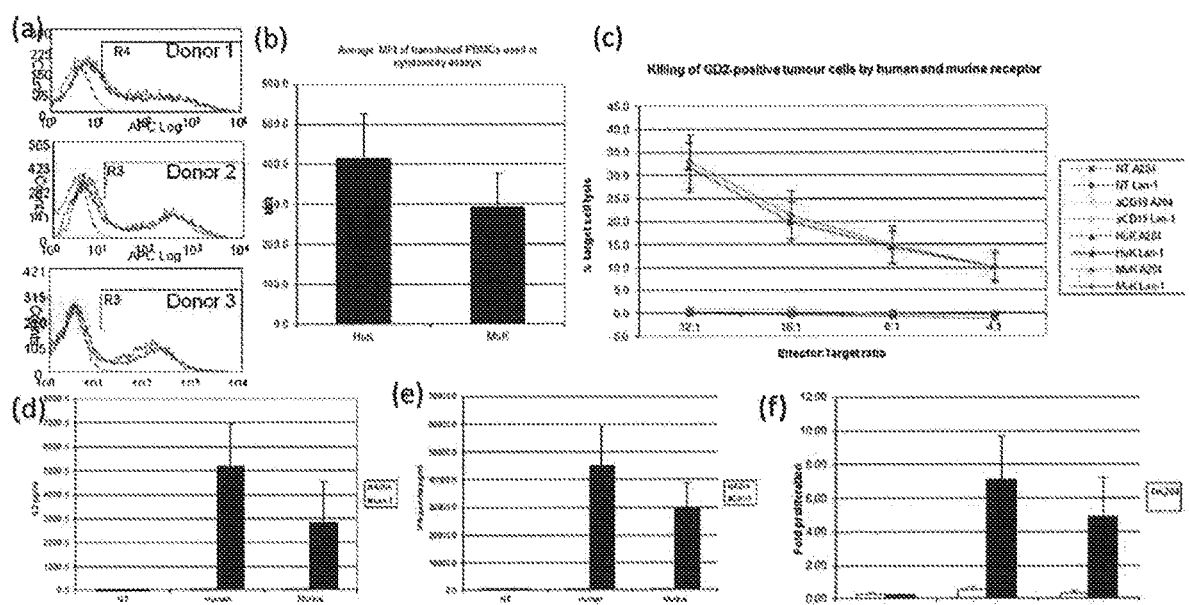
FIG. 3—Comparison of muKM666 and huKM666 based CARs. (a) Expression on peripheral blood T-cells from 3 normal donors; (b) mean-fluorescent intensity of these facs plots shown as a histogram; (c) Chromium release assay using non-transduced, muKM666 and huKM666 transduced T-cells as effectors against A204 (GD2 negative), and LAN-1 (GD2 positive) targets; (d) IL-2 production from the same challenge; (e) Interferon-gamma production from the same challenge; and (f) Fold-proliferation from the same challenge.

CARs were constructed with scFvs using sequences from either the mouse antibody KM666 or its humanized version huK666 as described by Nakamura et al (2001—as above) (variants (a) and (b) in FIG. 2 above). These receptors were compared for expression/stability and found to be equal for both receptors. Next, killing, cytokine release and proliferation of T-cells transduced with these receptors were tested when challenged by target cells either not expressing or expressing GD2. It was concluded that killing of both receptors was similar, but the humanized scFv based receptor resulted in superior IL2 production and proliferation (FIG. 3).

Example 2

Figure 4:
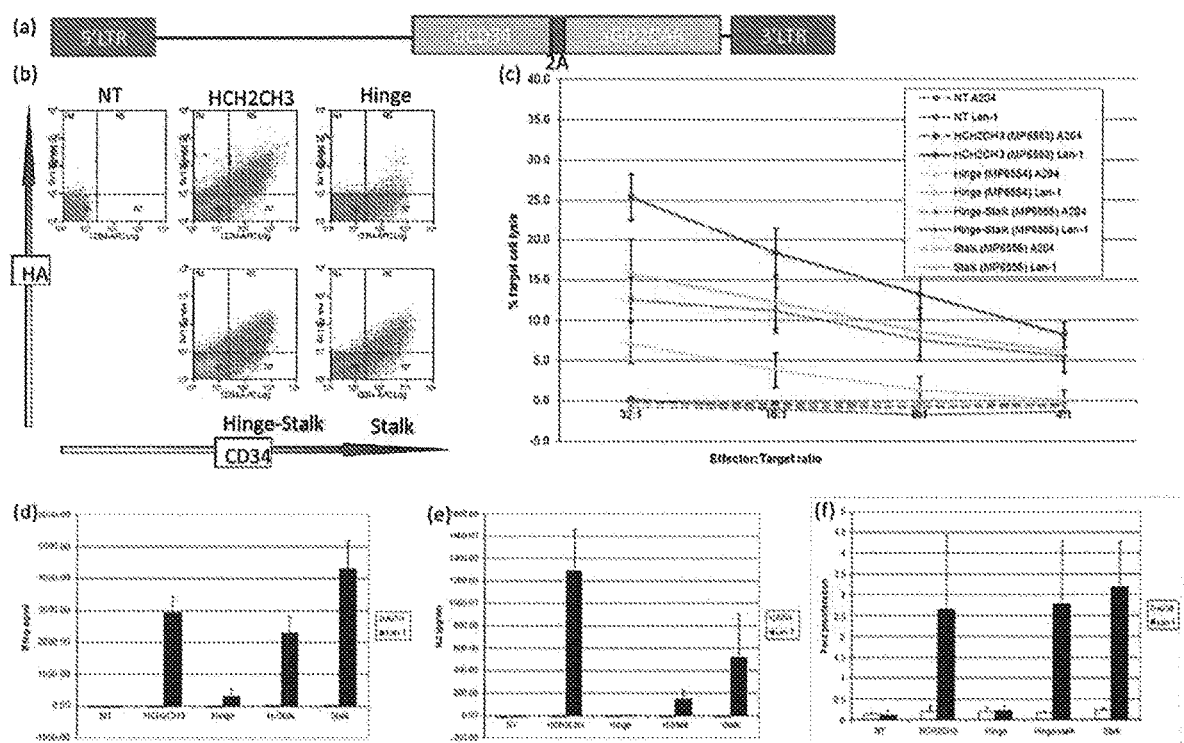
FIG. 4. (a) Retroviral construct allowing 1:1 co-expression of CD34 marker gene with CAR; (b) Flow cytometric analysis of CAR expression (HA tag) vs CD34 marker gene; (c) Chromium release assay of non-transduced T-cells and T-cells transduced with the 3 different CAR variants against GD2 positive targets (LAN-1), and GD2 negative targets (A204); (d) Interferon gamma release; (e) IL-2 release; and (f) proliferation of the same targets and effectors.

Testing the Effect of Different Spacer Formats Effects on Expression and Function Anti-GD2 CARs with Fc spacer, Hinge, Hinge-CD8 stalk and Cd8 stalk were generated (FIGS. 2(b), (d), (e) and (f) respectively). These CARs were co-expressed with the marker gene, truncated CD34, in an obligate 1:1 fashion with the 2A foot-and-mouth self-cleaving peptide to allow accurate comparison (FIG. 4a). Further, the huK666 scFv was tagged with an aminoterminal HA tag to allow comparison of transgene versus CAR expression.

Flow cytometric analysis of normal donor T-cells transduced with these constructs demonstrated brighter CAR expression in the following order: Fc>Hinge-stalk=stalk>Hinge (FIG. 4b).

Killing of GD2 positive targets relative to GD2 negative targets was compared using chromium release assays. This showed killing effectiveness in the following order: Fc>Hinge-stalk=stalk>Hinge (FIG. 4c).

Interferon-gamma release and IL-2 release was compared when CAR T-cells were challenged with either GD2 positive or negative targets. interferon-gamma release was similar in CARs with Fc, hinge-stalk and stalk but less in the hinge variant. IL2 release was detected in the following order: Fc, stalk, hinge-stalk, hinge (FIGS. 4d and e).

Finally, proliferation of CAR T-cells was compared when CAR T-cells were challenged with either GD2 positive or negative targets. Proliferation was detected in the following order: Stalk, hinge-stalk, Fc, hinge (FIGS. 4d and e).

Example 3

FcR Mutations Abrogate Non-Specific Activity

Figure 5:
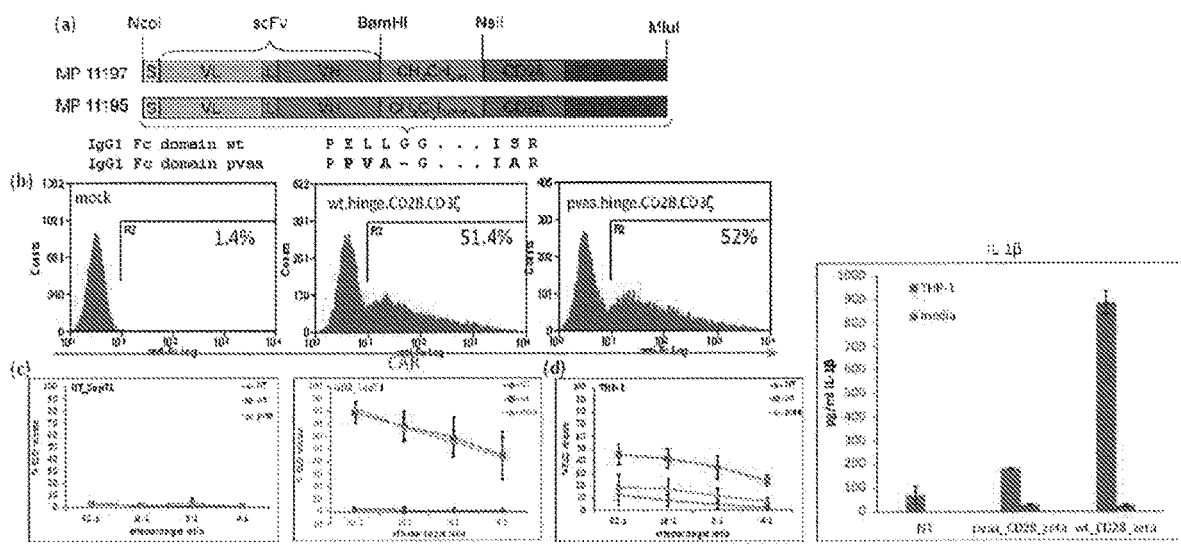
FIG. 5—Introduction of FcR binding disrupting mutations into the Fc spacer (a) mutations introduced; (b) Expression of CAR as determined by anti-Fc staining: nontransduced, wt and mutated; (c) Killing of GD2 negative and GD2 positive targets with either non-transduced, wt Fc and mutated Fc anti-GD2 CAR T-cells; (d) Activation of non-transduced, wt Fc and mutated Fc anti-GD2 T-cells with the FcR expressing cell line THP-1; IL-1Beta release by THP-1 cell line in response to non-transduced, wt Fc and mutated Fc CAR T-cells.

The overall data from the above Examples suggested that the Fc spacer performs best overall. However the Fc domain in vivo may lead to non-specific activation from cells which express Fc receptors. To abrogate this effect, mutations were introduced into the Fc region as shown in FIG. 5(a). These mutations had no deleterious effects on CAR expression, as shown in FIG. 5(b).

In addition, it was shown that these mutations had no effect on CAR killing function (FIG. 5(c)). Finally, it was shown that these mutations had the desired effect in terms of non-specific killing of FcR expressing targets (a monocytoid line called THP1), and IL-1 Beta release by these monocytes (FIG. 5e).

Example 4

Optimization of the Expression Cassette

With a view to optimising expression of the receptor, the following were tested: (a) inclusion of a scaffold attachment region (SAR) into the cassette; (b) inclusion of chicken beta hemoglobin chromatin insulator (CHS4) into the 3'LTR and (c) codon optimization of the open reading frame (FIG. 6a).

Figure 6:
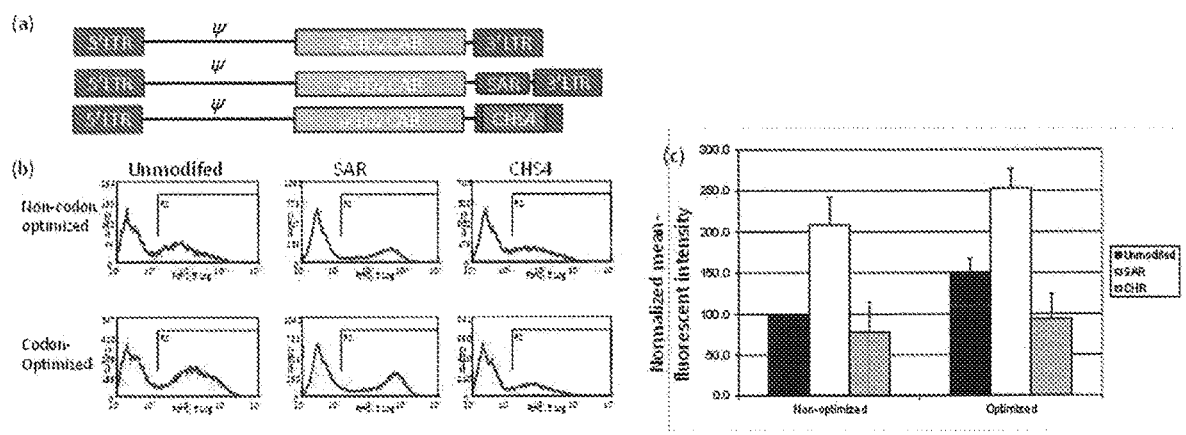
FIG. 6—Optimization of the Expression Cassette (a) map optimizations which were introduced into the cassette: SAR or CHS4; (b) representative expression of CAR with different modifications with either wt or codon-optimized open-reading frame. The SAR construct gives a tight peak of expression which is what is desired. (c) Bar chart representation of this FACS data from 3 normal donors.

It was shown that inclusion of a SAR improved the nature of expression as did codon-optimization while the CHS4 had little effect (FIG. 6b). Combining SAR and codon-optimization improved expression additively (FIG. 6c)

Example 5

Comparison of Different Endodomains

Figure 7:
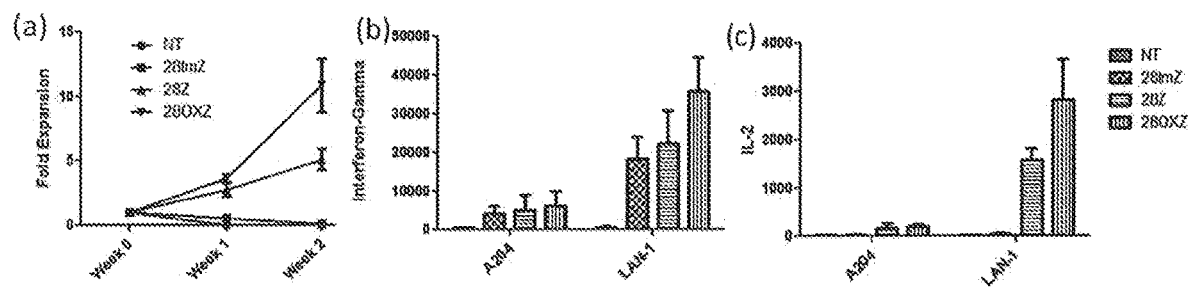
FIG. 7—Comparison of different endodomains

Constructs with three different endodomains were generated: CD28 trans-membrane domain with CD3-zeta endodomain (CD28tmZ); CD28 transmembrane domain with CD28 endodomain and CD3-zeta endodomain (CD28Z), and CD28 transmembrane domain, CD28 endodomain, OX30 endodomain and CD3-zeta endodomain (CD28OXZ) with a CAR in the Fc spacer format. Proliferation, IFNγ release and IL-2 release were noted to increase in order of CD28tmZ<CD28Z<CD28OXZ (FIG. 7).

Example 6

Co-Expression with iCasp9 Suicide Gene

The iCasp9 suicide gene was co-expressed with the anti-GD2 CAR (FIG. 8a—the CAR was in the format of Fc-spacer, CD28OXZ chosen arbitrarily to demonstrate function). The CAR could be well-expressed despite co-expression with iCasp9 (FIG. 8b). Activation of iCasp9 with the small molecular dimerizer led to deletion of CAR positive T-cells (FIG. 8b). iCasp9-GD2CAR T-cells exposed to this dimerizer lost their GD2 specificity when exposed to the dimerizer (FIG. 8c).

Example 7

Co-Expression with RQR8 Suicide Gene

The anti-GD2 CAR was co-expressed with the RQR8 sort-suicide gene. (FIG. 9a—the CAR was in the format of Fc-spacer, CD28Z chosen arbitrarily to demonstrate function). It was possible to co-express receptor and CAR (FIG. 9b). Activation of the suicide gene function of RQR8 with Rituximab and complement resulted in deletion of transduced T-cells and loss of GD2 recognition (FIGS. 9c and d).

Example 8

Expression of GD2 Synthase and GM3 Synthase Results in GD2 Expression in any Cell Line In order to stimulate GD2CAR T-cells in culture, to have ideal GD2-or GD2+targets, and to be able to generate syngeneic cells for small animal models, it is desirable to be able to transgenically express GD2 on a cell line. GD2 is not a protein and needs to be synthesized by a complex set of enzymes. Here it is shown that transgenic expression of just two enzymes: GM3synthase and GD2synthase results in bright GD2 expression in all cell lines transduced thus far (FIG. 10).

Example 9

In Vivo Function of Anti-GD2 CAR

CT26 cell line was engineered to express GD2 as described above (designated CT26 clone #7 or CT25#7 for short). Either $2 \times 10^5$ of wild type (wt) or GD2 positive CD26 cells were inoculated into the flanks of C57BL/6 mice (syngeneic with CT26). 10 days after tumour challenge, mock-transduced and anti-GD2 CAR transduced syngeneic splenocytes were prepared. Mice were divided into the following 4 cohorts: mice with GD2 expressing CT26 tumours receiving anti-GD2 CAR spleoncytes; GD2 expressing CT26 tumours receiving mock-transduced splenocytes; GD2 negative (wt) CT26 tumours with anti-GD2 CAR splenocytes; and GD2 expressing CT26 tumours receiving no splenocytes. Tumour was measured using a digital caliper in 3 dimension and volume estimated therewith. FIG. 11 shows the growth curves of the tumours. Only GD2 positive tumours in mice receiving anti-GD2 CAR T-cells had little or no growth.

Example 10

Comparing the Function of CARs Comprising huK666 and 14g2a-Based Antigen Binding Domains The antigen binding domain of a CAR can affect its function. In this study, the function of the CAR of the invention with an antigen-binding domain based on huK666 with a CAR was compared with an equivalent CAR having an antigen-binding domain based on 14g2a.

The antibody 14g2a can be seen as the gold standard antibody against GD2 since it is used as a therapeutic mAb and it is the only scFv tested in a CAR study.

Second generation CARs were constructed and expressed based on huK666 or 14g2a. Their structure is shown in FIG. 14a.

Retroviruses were produced by transient transfection of 293T cells with plasmids encoding the GD2 CARs, gag/pol and the envelope protein RD114. After 3 days the supernatants were harvested and used to transduce PHA/IL2-activated PBMCs with equal titres of retrovirus on retronectin-coated plates. The CARs differed solely in their antigen binding domain. In both cases the binding domains were linked to the membrane with an IgG Fc segment and contained intracellular activatory motifs from CD28 and CD3-zeta. Six days post-transduction CAR-expression was confirmed by flow cytometry and PBMCs were cultured in a 1:1 ratio with GD2-positive Lan1 cells (a GD2 positive cell line) or GD2-negative A204 cells (a GD2 negative rhabdomyosarcoma cell line). After one day supernatants from these co-cultures were assayed for interferon-γ levels by ELISA and T cell proliferation was assessed by flow cytometry after 6 days.

The results are shown in FIGS. 14 and 15. At 24 hours, Interferon-gamma was measured from supernatant. huK666 CAR T-cells were shown to produce more IFN-γ (FIG. 14b). After one week T-cells were counted, and the huK666 CAR was show to have more proliferation (FIG. 14c).

After one week of co-culture with the Neuroblastoma cell line LAN1, cells were harvested and analyzed by flow-cytometry. CD45 expression allowed discrimination from lymphoid cells and non-lymphoid cells with CD45− cells being LAN-1 cells. Further staining with CD3/QBEND/10 allowed counting of CAR T-cells. It was found that huK666 CAR T-cells proliferate better and kill more completely than 14g2a equivalents (FIG. 15).

All publications mentioned in the above specification are herein incorporated by reference. Various modifications and variations of the described methods and system of the invention will be apparent to those skilled in the art without departing from the scope and spirit of the invention.

Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A chimeric antigen receptor (CAR) comprising:
   a) a disialoganglioside (GD2)-binding domain and spacer, shown as amino acids 21 to 311 of SEQ ID NO: 29;
   b) a hydrophobic alpha helical transmembrane domain; and
   c) a CD28-CD3Zeta endodomain shown as SEQ ID NO: 17.

2. A chimeric antigen receptor (CAR) which comprises the sequence shown as any of SEQ ID NO: 27 to 29 and 31 to 35.

3. A nucleic acid sequence which encodes a CAR according to claim 2 or 1.

4. A nucleic acid according claim 3 which also encodes a suicide gene.

5. A nucleic acid sequence according to claim 3 which comprises the sequence shown as SEQ ID NO: 25 or a variant thereof having at least 90% sequence identity.

6. A vector which comprises a nucleic acid sequence according to claim 3.

7. A T cell which expresses a CAR according to claim 2 or 1.

8. A T cell which co-expresses a CAR according to claim 2 or 1 and a suicide gene.

9. A T cell according to claim 8, wherein the suicide gene is inducible Caspase 9 (iCasp9) or RQR8.

10. A method for making a T cell which expresses a CAR, which comprises the step of introducing a nucleic acid according to claim 3 ex vivo into a T cell.

11. A pharmaceutical composition which comprises a T cell according to claim 7, together with a pharmaceutically acceptable carrier, diluent or excipient.

12. A method for treating neuroblastoma which comprises the step of administering a T cell according to claim 7 to a subject.

13. A vector which comprises a nucleic acid sequence according to claim 4.

14. A pharmaceutical composition which comprises a vector according to claim 6, together with a pharmaceutically acceptable carrier, diluent or excipient.

15. A pharmaceutical composition which comprises a vector according to claim 13, together with a pharmaceutically acceptable carrier, diluent or excipient.

16. The pharmaceutical composition according to claim 15 wherein the suicide gene is inducible Caspase 9 (iCasp9) or RQR8.

17. A T cell according to claim 8 comprising the sequence shown as SEQ ID NO: 34 or 35.

* * * * *

```
                              SEQUENCE LISTING

<160> NUMBER OF SEQ ID NOS: 37

<210> SEQ ID NO 1
   <211> LENGTH: 5
   <212> TYPE: PRT
   <213> ORGANISM: Artificial Sequence
   <220> FEATURE:
   <223> OTHER INFORMATION: Heavy chain variable region CDR1

<400> SEQUENCE: 1

Ser Tyr Asn Ile His
   1               5

<210> SEQ ID NO 2
   <211> LENGTH: 16
   <212> TYPE: PRT
   <213> ORGANISM: Artificial Sequence
   <220> FEATURE:
   <223> OTHER INFORMATION: Heavy chain variable region CDR2

<400> SEQUENCE: 2

Val Ile Trp Ala Gly Gly Ser Thr Asn Tyr Asn Ser Ala Leu Met Ser
   1               5                   10                  15

<210> SEQ ID NO 3
   <211> LENGTH: 10
   <212> TYPE: PRT
   <213> ORGANISM: Artificial Sequence
   <220> FEATURE:
   <223> OTHER INFORMATION: Heavy chain variable region CDR3

<400> SEQUENCE: 3

Arg Ser Asp Asp Tyr Ser Trp Phe Ala Tyr
   1               5                   10

<210> SEQ ID NO 4
   <211> LENGTH: 12
   <212> TYPE: PRT
   <213> ORGANISM: Artificial Sequence
   <220> FEATURE:
   <223> OTHER INFORMATION: Light chain variable region CDR1

<400> SEQUENCE: 4

Arg Ala Ser Ser Ser Val Ser Ser Ser Tyr Leu His
   1               5                   10

<210> SEQ ID NO 5
   <211> LENGTH: 7
   <212> TYPE: PRT
   <213> ORGANISM: Artificial Sequence
   <220> FEATURE:
   <223> OTHER INFORMATION: Light chain variable region CDR2

<400> SEQUENCE: 5

Ser Thr Ser Asn Leu Ala Ser
   1               5

<210> SEQ ID NO 6
   <211> LENGTH: 9
   <212> TYPE: PRT
   <213> ORGANISM: Artificial Sequence
   <220> FEATURE:
```

-continued

<223> OTHER INFORMATION: Light chain variable region CDR3

<400> SEQUENCE: 6

Gln Gln Tyr Ser Gly Tyr Pro Ile Thr
1               5

<210> SEQ ID NO 7
<211> LENGTH: 243
<212> TYPE: PRT
<213> ORGANISM: Artificial Sequence
<220> FEATURE:
<223> OTHER INFORMATION: Murine KM666 sequence

<400> SEQUENCE: 7

Gln Val Gln Leu Lys Glu Ser Gly Pro Val Leu Val Ala Pro Ser Gln
1               5                   10                  15

Thr Leu Ser Ile Thr Cys Thr Val Ser Gly Phe Ser Leu Ala Ser Tyr
            20                  25                  30

Asn Ile His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Gln Met Asn Ser Leu Gln Thr Asp Asp Thr Ala Met Tyr Tyr Cys Ala
                85                  90                  95

Lys Arg Ser Asp Asp Tyr Ser Trp Phe Ala Tyr Trp Gly Gln Gly Thr
            100                 105                 110

Leu Val Thr Val Ser Ala Ser Gly Gly Gly Ser Gly Gly Gly Gly
        115                 120                 125

Ser Gly Gly Gly Gly Ser Glu Asn Val Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Ser Ser Tyr Leu His Trp Tyr Gln Gln Lys Ser Gly
                165                 170                 175

Ala Ser Pro Lys Val Trp Ile Tyr Ser Thr Ser Asn Leu Ala Ser Gly
            180                 185                 190

Val Pro Gly Arg Phe Ser Gly Ser Gly Ser Gly Thr Ser Tyr Ser Leu
        195                 200                 205

Thr Ile Ser Ser Val Glu Ala Glu Asp Ala Ala Thr Tyr Tyr Cys Gln
    210                 215                 220

Gln Tyr Ser Gly Tyr Pro Ile Thr Phe Gly Ala Gly Thr Lys Val Glu
225                 230                 235                 240

Val Lys Arg

<210> SEQ ID NO 8
<211> LENGTH: 242
<212> TYPE: PRT
<213> ORGANISM: Artificial Sequence
<220> FEATURE:
<223> OTHER INFORMATION: Humanised KM666 sequence

<400> SEQUENCE: 8

Gln Val Gln Leu Gln Glu Ser Gly Pro Gly Leu Val Lys Pro Ser Gln
1               5                   10                  15

Thr Leu Ser Ile Thr Cys Thr Val Ser Gly Phe Ser Leu Ala Ser Tyr
            20                  25                  30

Asn Ile His Trp Val Arg Gln Pro Pro Gly Lys Gly Leu Glu Trp Leu
            35                  40                  45

Gly Val Ile Trp Ala Gly Gly Ser Thr Asn Tyr Asn Ser Ala Leu Met
 50                  55                  60

Ser Arg Leu Thr Ile Ser Lys Asp Asn Ser Lys Asn Gln Val Phe Leu
 65                  70                  75                  80

Lys Met Ser Ser Leu Thr Ala Ala Asp Thr Ala Val Tyr Tyr Cys Ala
                 85                  90                  95

Lys Arg Ser Asp Asp Tyr Ser Trp Phe Ala Tyr Trp Gly Gln Gly Thr
                100                 105                 110

Leu Val Thr Val Ser Ser Gly Gly Gly Ser Gly Gly Gly Ser
            115                 120                 125

Gly Gly Gly Gly Ser Glu Asn Gln Met Thr Gln Ser Pro Ser Ser Leu
            130                 135                 140

Ser Ala Ser Val Gly Asp Arg Val Thr Met Thr Cys Arg Ala Ser Ser
145                 150                 155                 160

Ser Val Ser Ser Ser Tyr Leu His Trp Tyr Gln Gln Lys Ser Gly Lys
                165                 170                 175

Ala Pro Lys Val Trp Ile Tyr Ser Thr Ser Asn Leu Ala Ser Gly Val
            180                 185                 190

Pro Ser Arg Phe Ser Gly Ser Gly Ser Gly Thr Asp Tyr Thr Leu Thr
            195                 200                 205

Ile Ser Ser Leu Gln Pro Glu Asp Phe Ala Thr Tyr Tyr Cys Gln Gln
            210                 215                 220

Tyr Ser Gly Tyr Pro Ile Thr Phe Gly Gln Gly Thr Lys Val Glu Ile
225                 230                 235                 240

Lys Arg

<210> SEQ ID NO 9
<211> LENGTH: 118
<212> TYPE: PRT
<213> ORGANISM: Artificial Sequence
<220> FEATURE:
<223> OTHER INFORMATION: Murine KM666 VH (heavy chain variable region)
      sequence

<400> SEQUENCE: 9

Gln Val Gln Leu Lys Glu Ser Gly Pro Val Leu Val Ala Pro Ser Gln
 1               5                  10                  15

Thr Leu Ser Ile Thr Cys Thr Val Ser Gly Phe Ser Leu Ala Ser Tyr
            20                  25                  30

Asn Ile His Trp Val Arg Gln Pro Pro Gly Lys Gly Leu Glu Trp Leu
            35                  40                  45

Gly Val Ile Trp Ala Gly Gly Ser Thr Asn Tyr Asn Ser Ala Leu Met
 50                  55                  60

Ser Arg Leu Ser Ile Ser Lys Asp Asn Ser Lys Ser Gln Val Phe Leu
 65                  70                  75                  80

Gln Met Asn Ser Leu Gln Thr Asp Asp Thr Ala Met Tyr Tyr Cys Ala
                 85                  90                  95

Lys Arg Ser Asp Asp Tyr Ser Trp Phe Ala Tyr Trp Gly Gln Gly Thr
                100                 105                 110

Leu Val Thr Val Ser Ala
            115

<210> SEQ ID NO 10

<211> LENGTH: 118
<212> TYPE: PRT
<213> ORGANISM: Artificial Sequence
<220> FEATURE:
<223> OTHER INFORMATION: Humanised KM666 VH sequence

<400> SEQUENCE: 10

Gln Val Gln Leu Gln Glu Ser Gly Pro Gly Leu Val Lys Pro Ser Gln
1               5                   10                  15

Thr Leu Ser Ile Thr Cys Thr Val Ser Gly Phe Ser Leu Ala Ser Tyr
            20                  25                  30

Asn Ile His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Thr Ile Ser Lys Asp Asn Ser Lys Asn Gln Val Phe Leu
65                  70                  75                  80

Lys Met Ser Ser Leu Thr Ala Ala Asp Thr Ala Val Tyr Tyr Cys Ala
                85                  90                  95

Lys Arg Ser Asp Asp Tyr Ser Trp Phe Ala Tyr Trp Gly Gln Gly Thr
            100                 105                 110

Leu Val Thr Val Ser Ser
        115

<210> SEQ ID NO 11
<211> LENGTH: 108
<212> TYPE: PRT
<213> ORGANISM: Artificial Sequence
<220> FEATURE:
<223> OTHER INFORMATION: Murine KM666 VL (light chain variable region)
      sequence

<400> SEQUENCE: 11

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Val Trp
        35                  40                  45

Ile Tyr Ser Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Ile Thr Phe Gly Ala Gly Thr Lys Val Glu Val Lys
            100                 105

<210> SEQ ID NO 12
<211> LENGTH: 108
<212> TYPE: PRT
<213> ORGANISM: Artificial Sequence
<220> FEATURE:
<223> OTHER INFORMATION: Humanised KM666 VL sequence

<400> SEQUENCE: 12

Glu Asn Gln Met Thr Gln Ser Pro Ser Ser Leu Ser Ala Ser Val Gly
1               5                   10                  15

Asp Arg Val Thr Met Thr Cys Arg Ala Ser Ser Ser Val Ser Ser Ser
            20                  25                  30

Tyr Leu His Trp Tyr Gln Gln Lys Ser Gly Lys Ala Pro Lys Val Trp
            35                  40                  45

Ile Tyr Ser Thr Ser Asn Leu Ala Ser Gly Val Pro Ser Arg Phe Ser
 50                  55                  60

Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys Gln Gln Tyr Ser Gly Tyr Pro
                 85                  90                  95

Ile Thr Phe Gly Gln Gly Thr Lys Val Glu Ile Lys
            100                 105

<210> SEQ ID NO 13
<211> LENGTH: 27
<212> TYPE: PRT
<213> ORGANISM: Artificial Sequence
<220> FEATURE:
<223> OTHER INFORMATION: Transmembrane domain

<400> SEQUENCE: 13

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 14
<211> LENGTH: 39
<212> TYPE: PRT
<213> ORGANISM: Artificial Sequence
<220> FEATURE:
<223> OTHER INFORMATION: CD28 endodomain

<400> SEQUENCE: 14

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr
        35

<210> SEQ ID NO 15
<211> LENGTH: 38
<212> TYPE: PRT
<213> ORGANISM: Artificial Sequence
<220> FEATURE:
<223> OTHER INFORMATION: CD40 endodomain

<400> SEQUENCE: 15

Arg Ser Arg Asp Gln Arg Leu Pro Pro Asp Ala His Lys Pro Pro Gly
1               5                   10                  15

Gly Gly Ser Phe Arg Thr Pro Ile Gln Glu Glu Gln Ala Asp Ala His
            20                  25                  30

Ser Thr Leu Ala Lys Ile
        35

<210> SEQ ID NO 16
<211> LENGTH: 114
<212> TYPE: PRT
<213> ORGANISM: Artificial Sequence
<220> FEATURE:
<223> OTHER INFORMATION: CD3 zeta endodomain

<400> SEQUENCE: 16

```
Arg Ser Arg Val Lys Phe Ser Arg Ser Ala Asp Ala Pro Ala Tyr Gln
1               5                   10                  15

Gln Gly Gln Asn Gln Leu Tyr Asn Glu Leu Asn Leu Gly Arg Arg Glu
            20                  25                  30

Glu Tyr Asp Val Leu Asp Lys Arg Arg Gly Arg Asp Pro Glu Met Gly
        35                  40                  45

Gly Lys Pro Arg Arg Lys Asn Pro Gln Glu Gly Leu Tyr Asn Glu Leu
    50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg

<210> SEQ ID NO 17
<211> LENGTH: 153
<212> TYPE: PRT
<213> ORGANISM: Artificial Sequence
<220> FEATURE:
<223> OTHER INFORMATION: CD28Z

<400> SEQUENCE: 17

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Arg Val Lys Phe Ser Arg Ser
        35                  40                  45

Ala Asp Ala Pro Ala Tyr Gln Gln Gly Gln Asn Gln Leu Tyr Asn Glu
    50                  55                  60

Leu Asn Leu Gly Arg Arg Glu Glu Tyr Asp Val Leu Asp Lys Arg Arg
65                  70                  75                  80

Gly Arg Asp Pro Glu Met Gly Gly Lys Pro Arg Arg Lys Asn Pro Gln
                85                  90                  95

Glu Gly Leu Tyr Asn Glu Leu Gln Lys Asp Lys Met Ala Glu Ala Tyr
            100                 105                 110

Ser Glu Ile Gly Met Lys Gly Glu Arg Arg Arg Gly Lys Gly His Asp
        115                 120                 125

Gly Leu Tyr Gln Gly Leu Ser Thr Ala Thr Lys Asp Thr Tyr Asp Ala
    130                 135                 140

Leu His Met Gln Ala Leu Pro Pro Arg
145                 150

<210> SEQ ID NO 18
<211> LENGTH: 189
<212> TYPE: PRT
<213> ORGANISM: Artificial Sequence
<220> FEATURE:
<223> OTHER INFORMATION: CD28OXZ

<400> SEQUENCE: 18

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30
```

```
Pro Arg Asp Phe Ala Ala Tyr Arg Ser Arg Asp Gln Arg Leu Pro Pro
            35                  40                  45

Asp Ala His Lys Pro Pro Gly Gly Ser Phe Arg Thr Pro Ile Gln
 50                  55                  60

Glu Glu Gln Ala Asp Ala His Ser Thr Leu Ala Lys Ile Arg Val Lys
 65                  70                  75                  80

Phe Ser Arg Ser Ala Asp Ala Pro Ala Tyr Gln Gln Gly Gln Asn Gln
                 85                  90                  95

Leu Tyr Asn Glu Leu Asn Leu Gly Arg Arg Glu Glu Tyr Asp Val Leu
             100                 105                 110

Asp Lys Arg Arg Gly Arg Asp Pro Glu Met Gly Gly Lys Pro Arg Arg
             115                 120                 125

Lys Asn Pro Gln Glu Gly Leu Tyr Asn Glu Leu Gln Lys Asp Lys Met
 130                 135                 140

Ala Glu Ala Tyr Ser Glu Ile Gly Met Lys Gly Glu Arg Arg Arg Gly
 145                 150                 155                 160

Lys Gly His Asp Gly Leu Tyr Gln Gly Leu Ser Thr Ala Thr Lys Asp
                 165                 170                 175

Thr Tyr Asp Ala Leu His Met Gln Ala Leu Pro Pro Arg
             180                 185

<210> SEQ ID NO 19
<211> LENGTH: 20
<212> TYPE: PRT
<213> ORGANISM: Artificial Sequence
<220> FEATURE:
<223> OTHER INFORMATION: Signal peptide

<400> SEQUENCE: 19

Met Glu Thr Asp Thr Leu Leu Leu Trp Val Leu Leu Leu Trp Val Pro
 1               5                  10                  15

Gly Ser Thr Gly
             20

<210> SEQ ID NO 20
<211> LENGTH: 234
<212> TYPE: PRT
<213> ORGANISM: Artificial Sequence
<220> FEATURE:
<223> OTHER INFORMATION: Hinge-CH2CH3 of human IgG1 spacer

<400> SEQUENCE: 20

Ala Glu Pro Lys Ser Pro Asp Lys Thr His Thr Cys Pro Pro Cys Pro
 1               5                  10                  15

Ala Pro Pro Val Ala Gly Pro Ser Val Phe Leu Phe Pro Pro Lys Pro
                 20                  25                  30

Lys Asp Thr Leu Met Ile Ala Arg Thr Pro Glu Val Thr Cys Val Val
             35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
             100                 105                 110

Leu Pro Ala Pro Ile Glu Lys Thr Ile Ser Lys Ala Lys Gly Gln Pro
```

```
                        115                 120                 125
Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp
225                 230

<210> SEQ ID NO 21
<211> LENGTH: 46
<212> TYPE: PRT
<213> ORGANISM: Artificial Sequence
<220> FEATURE:
<223> OTHER INFORMATION: Human CD8 stalk spacer

<400> SEQUENCE: 21

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile
            35                  40                  45

<210> SEQ ID NO 22
<211> LENGTH: 20
<212> TYPE: PRT
<213> ORGANISM: Artificial Sequence
<220> FEATURE:
<223> OTHER INFORMATION: Human IgG1 hinge spacer

<400> SEQUENCE: 22

Ala Glu Pro Lys Ser Pro Asp Lys Thr His Thr Cys Pro Pro Cys Pro
1               5                   10                  15

Lys Asp Pro Lys
                20

<210> SEQ ID NO 23
<211> LENGTH: 237
<212> TYPE: PRT
<213> ORGANISM: Artificial Sequence
<220> FEATURE:
<223> OTHER INFORMATION: IgG1 Hinge-Fc spacer

<400> SEQUENCE: 23

Ala Glu Pro Lys Ser Pro Asp Lys Thr His Thr Cys Pro Pro Cys Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
        50                  55                  60
```

```
Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Lys Asp Pro Lys
225                 230                 235

<210> SEQ ID NO 24
<211> LENGTH: 236
<212> TYPE: PRT
<213> ORGANISM: Artificial Sequence
<220> FEATURE:
<223> OTHER INFORMATION: IgG1 Hinge spacer - Fc modified to remove Fc
      receptor recognition motifs

<400> SEQUENCE: 24

Ala Glu Pro Lys Ser Pro Asp Lys Thr His Thr Cys Pro Pro Cys Pro
 1               5                  10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
```

```
            180                 185                 190
Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Lys Lys Asp Pro Lys
225                 230                 235

<210> SEQ ID NO 25
<211> LENGTH: 6014
<212> TYPE: DNA
<213> ORGANISM: Artificial Sequence
<220> FEATURE:
<223> OTHER INFORMATION: Retroviral cassette

<400> SEQUENCE: 25
tgaaagaccc cacctgtagg tttggcaagc tagcttaagt aacgccattt tgcaaggcat      60
ggaaaaatac ataactgaga atagaaaagt tcagatcaag gtcaggaaca gatggaacag     120
ctgaatatgg gccaaacagg atatctgtgg taagcagttc ctgccccggc tcagggccaa     180
gaacagatga acagctgaa tatgggccaa acaggatatc tgtggtaagc agttcctgcc      240
ccggctcagg gccaagaaca gatggtcccc agatgcggtc cagccctcag cagtttctag     300
agaaccatca gatgtttcca gggtgcccca aggacctgaa atgaccctgt gccttatttg     360
aactaaccaa tcagttcgct tctcgcttct gttcgcgcgc ttatgctccc cgagctcaat     420
aaaagagccc acaacccctc actcggggcg ccagtcctcc gattgactga gtcgcccggg     480
tacccgtgta tccaataaac cctcttgcag ttgcatccga cttgtggtct cgctgttcct     540
tgggagggtc tcctctgagt gattgactac ccgtcagcgg gggtcttttca tttgggggct     600 cgtccgggat cgggagaccc ctgcccaggg accaccgacc caccacccgg aggtaagctg     660
gccagcaact tatctgtgtc tgtccgattg tctagtgtct atgactgatt ttatgcgcct     720
gcgtcggtac tagttagcta actagctctg tatctggcgg acccgtggtg gaactgacga     780
gttcggaaca cccggccgca accctgggag acgtcccagg gacttcgggg gccgttttg     840 tggcccgacc tgagtcctaa aatcccgatc gtttaggact ctttggtgca cccccttag     900 aggagggata tgtggttctg gtaggagacg agaacctaaa acagttcccg cctccgtctg     960
aatttttgct ttcggtttgg gaccgaagcc gcgccgcgcg tcttgtctgc tgcagcatcg    1020
ttctgtgttg tctctgtctg actgtgtttc tgtatttgtc tgaaaatatg ggcccgggct    1080
agcctgttac cactccctta agttgacct taggtcactg gaaagatgtc gagcggatcg    1140
ctcacaacca gtcggtagat gtcaagaaga gacgttgggt taccttctgc tctgcagaat    1200
ggccaacctt taacgtcgga tggccgcgag acggcacctt taaccgagac ctcatcaccc    1260
aggttaagat caaggtcttt tcacctggcc cgcatggaca cccagaccag gtggggtaca    1320
tcgtgacctg ggaagccttg gcttttgacc ccctccctg ggtcaagccc tttgtacacc    1380
ctaagcctcc gcctcctctt cctccatccg ccccgtctct cccccttgaa cctcctcgtt    1440
cgaccccgcc tcgatcctcc ctttatccag ccctcactcc ttctctaggc gccccatat    1500 ggccatatga gatcttatat ggggcacccc cgccccttgt aaacttcccct gaccctgaca    1560 tgacaagagt tactaacagc ccctctctcc aagctcactt acaggctctc tacttagtcc    1620
agcacgaagt ctggagacct ctggcggcag cctaccaaga caactggac cgaccggtgg    1680 tacctcaccc ttaccgagtc ggcgacacag tgtgggtccg ccgacaccag actaagaacc    1740
```

```
tagaacctcg ctggaaagga ccttacacag tcctgctgac cacccccacc gccctcaaag   1800
tagacggcat cgcagcttgg atacacgccg cccacgtgaa ggctgccgac cccggggtg    1860 gaccatcctc tagactgcca acatgggcac cagcctgctg tgctggatgg ccctgtgcct   1920
gctgggcgcc gaccacgccg atgcctgccc ctacagcaac cccagcctgt gcagcggagg   1980
cggcggcagc gagctgccca cccagggcac cttctccaac gtgtccacca acgtgagccc   2040
agccaagccc accaccaccg cctgtcctta ttccaatcct tccctgtgta gcggaggggg   2100
aggcagccca gcccccagac ctcccacccc agcccccacc atcgccagcc agcctctgag   2160
cctgagaccc gaggcctgcc gcccagccgc cggcggcgcc gtgcacacca gaggcctgga   2220
tttcgcctgc gatatctaca tctgggcccc actggccggc acctgtggcg tgctgctgct   2280
gagcctggtg atcaccctgt actgcaacca ccgcaaccgc aggcgcgtgt gcaagtgccc   2340
caggcccgtg gtgagagccg agggcagagg cagcctgctg acctgcggcg acgtggagga   2400
gaacccaggc cccatggaga ccgacaccct gctgctgtgg gtgctgctgc tgtgggtgcc   2460
aggcagcacc ggccaggtgc agctgcagga gtctggccca ggcctggtga agccagcca   2520 gacccctgagc atcacctgca ccgtgagcgg cttcagcctg gccagctaca acatccactg   2580
ggtgcggcag ccccaggca agggcctgga gtggctgggc gtgatctggg ctggcggcag   2640
caccaactac aacagcgccc tgatgagccg gctgaccatc agcaaggaca acagcaagaa   2700
ccaggtgttc ctgaagatga gcagcctgac agccgccgac accgccgtgt actactgcgc   2760
caagcggagc gacgactaca gctggttcgc ctactggggc cagggcaccc tggtgaccgt   2820
gagctctggc ggaggcggct ctggcggagg cggctctggc ggaggcggca gcgagaacca   2880
gatgacccag agcccagca gcttgagcgc cagcgtgggc gaccgggtga ccatgacctg   2940
cagagccagc agcagcgtga gcagcagcta cctgcactgg taccagcaga gagcggcaa   3000 ggcccccaaag gtgtggatct acagcaccag caacctggcc agcggcgtgc cagccggtt   3060 cagcggcagc ggcagcggca ccgactacac cctgaccatc agcagcctgc agcccgagga   3120
cttcgccacc tactactgcc agcagtacag cggctacccc atcaccttcg gccagggcac   3180
caaggtggag atcaagcggt cggatcccgc cgagcccaaa tctcctgaca aaactcacac   3240
atgcccaccg tgcccagcac ctccgtggc cggccgtca gtcttcctct tccccccaaa   3300
acccaaggac accctcatga tcgcccggac ccctgaggtc acatgcgtgg tggtggacgt   3360
gagccacgaa gaccctgagg tcaagttcaa ctggtacgtg gacggcgtgg aggtgcataa   3420
tgccaagaca aagccgcggg aggagcagta caacagcacg taccgtgtgg tcagcgtcct   3480
caccgtcctg caccaggact ggctgaatgg caaggagtac aagtgcaagg tctccaacaa   3540
agccctccca gcccccatcg agaaaaccat ctccaaagcc aaagggcagc ccgagaacc   3600 acaggtgtac accctgcccc catcccggga tgagctgacc aagaaccagg tcagcctgac   3660
ctgcctggtc aaaggcttct atcccagcga catcgccgtg gagtgggaga gcaatgggca   3720
accggagaac aactacaaga ccacgcctcc cgtgctggac tccgacggct ccttcttcct   3780
ctacagcaag ctcaccgtgg acaagagcag gtggcagcag gggaacgtct tctcatgctc   3840
cgtgatgcat gaggccctgc acaatcacta cacccagaaa tctctgagtc tgagcccagg   3900
caagaaggac cccaagttct gggtcctggt ggtggtggga ggcgtgctgg cctgttactc   3960
tctcctggtg accgtggcct tcatcatctt ctgggtgcgc tccaagagga gcaggctcct   4020
gcacagtgac tacatgaaca tgactccccg ccgccccggg cccacccgca agcattacca   4080
gccctatgcc ccaccacgcg acttcgcagc ctatcgctcc cgggtgaagt tctctcgctc   4140
```

-continued

```
tgccgatgcc ccagcctatc agcagggcca gaatcagctg tacaatgaac tgaacctggg      4200
caggcgggag gagtacgacg tgctggataa gcggagaggc agagaccccg agatgggcgg      4260
caaaccacgg cgcaaaaatc cccaggaggg actctataac gagctgcaga aggacaaaat      4320
ggccgaggcc tattccgaga tcggcatgaa gggagagaga gacgcggaa agggccacga       4380 cggcctgtat cagggattgt ccaccgctac aaaagataca tatgatgccc tgcacatgca      4440
ggccctgcca cccagatgac gcgtatcgat actgttctca tcacatcata tcaaggttat      4500
ataccatcaa tattgccaca gatgttactt agccttttaa tatttctcta atttagtgta      4560
tatgcaatga tagttctctg atttctgaga ttgagtttct catgtgtaat gattatttag      4620
agtttctctt tcatctgttc aaattttgt ctagtttat tttttactga tttgtaagac        4680
ttctttttat aatctgcata ttacaattct ctttactggg gtgttgcaaa tattttctgt      4740
cattctatgg cctgactttt cttaatggtt ttaatttt aaaaataagt cttaatattc         4800
atgcaatcta attaacaatc tttctttgt ggttaggact tgagtcata agaaattttt         4860 ctctacactg aagtcatgat ggcatgcttc tatattattt tctaaaagat ttaaagtttt      4920
gccttctcca tttagactta taattcactg gaattttttt gtgtgtatgg tatgacatat      4980
gggttccctt ttatttttta catataaata tatttccctg tttttctaaa aagaaaaag       5040 atcatcattt tcccattgta aaatgccata ttttttcat aggtcactta catatatcaa       5100
tgggtctgtt tctgagctct actctatttt atcagcctca ctgtctatcc ccacacatct      5160
catgctttgc tctaaatctt gatatttagt ggaacattct ttcccatttt gttctacaag      5220 aatattttg ttattgtctt tgggctttct atatacattt tgaaatgagg ttgacaagtt       5280
cggattagtc caatttgtta aagacaggat atcagtggtc caggctctag ttttgactca      5340
acaatatcac cagctgaagc ctatagagta cgagccatag ataaaataaa agatttatt       5400 tagtctccag aaaaagggg gaatgaaaga ccccacctgt aggtttggca agctagctta       5460
agtaacgcca ttttgcaagg catggaaaaa tacataactg agaatagaga agttcagatc      5520
aaggtcagga acagatggaa cagctgaata tgggccaaac aggatatctg tggtaagcag      5580
ttcctgcccc ggctcagggc caagaacaga tggaacagct gaatatgggc caaacaggat      5640
atctgtggta agcagttcct gccccggctc agggccaaga acagatggtc cccagatgcg      5700
gtccagccct cagcagtttc tagagaacca tcagatgttt ccagggtgcc caaggacct      5760 gaaatgaccc tgtgccttat ttgaactaac caatcagttc gcttctcgct tctgttcgcg      5820
cgcttctgct ccccgagctc aataaaaagag cccacaaccc ctcactcggg gcgccagtcc     5880
tccgattgac tgagtcgccc gggtacccgt gtatccaata aaccctcttg cagttgcatc      5940
cgacttgtgg tctcgctgtt ccttgggagg gtctcctctg agtgattgac tacccgtcag      6000
cgggggtctt tcac                                                       6014
```

<210> SEQ ID NO 26
<211> LENGTH: 719
<212> TYPE: PRT
<213> ORGANISM: Artificial Sequence
<220> FEATURE:
<223> OTHER INFORMATION: anti-GD2 CAR, muKM666-HCH2CH3-CD28OXZ

<400> SEQUENCE: 26

Met Glu Thr Asp Thr Leu Leu Leu Trp Val Leu Leu Leu Trp Val Pro
1               5                   10                  15

Gly Ser Thr Gly Gln Val Gln Leu Lys Glu Ser Gly Pro Val Leu Val

```
            20                  25                  30
Ala Pro Ser Gln Thr Leu Ser Ile Thr Cys Thr Val Ser Gly Phe Ser
            35                  40                  45
Leu Ala Ser Tyr Asn Ile His Trp Val Arg Gln Pro Pro Gly Lys Gly
            50                  55                  60
Leu Glu Trp Leu Gly Val Ile Trp Ala Gly Gly Ser Thr Asn Tyr Asn
65                  70                  75                  80
Ser Ala Leu Met Ser Arg Leu Ser Ile Ser Lys Asp Asn Ser Lys Ser
                85                  90                  95
Gln Val Phe Leu Gln Met Asn Ser Leu Gln Thr Asp Asp Thr Ala Met
                100                 105                 110
Tyr Tyr Cys Ala Lys Arg Ser Asp Asp Tyr Ser Trp Phe Ala Tyr Trp
                115                 120                 125
Gly Gln Gly Thr Leu Val Thr Val Ser Ala Ser Gly Gly Gly Gly Ser
                130                 135                 140
Gly Gly Gly Gly Ser Gly Gly Gly Ser Glu Asn Val Leu Thr Gln
145                 150                 155                 160
Ser Pro Ala Ile Met Ser Ala Ser Pro Gly Glu Lys Val Thr Met Thr
                165                 170                 175
Cys Arg Ala Ser Ser Val Ser Ser Ser Tyr Leu His Trp Tyr Gln
                180                 185                 190
Gln Lys Ser Gly Ala Ser Pro Lys Val Trp Ile Tyr Ser Thr Ser Asn
                195                 200                 205
Leu Ala Ser Gly Val Pro Gly Arg Phe Ser Gly Ser Gly Ser Gly Thr
                210                 215                 220
Ser Tyr Ser Leu Thr Ile Ser Ser Val Glu Ala Glu Asp Ala Ala Thr
225                 230                 235                 240
Tyr Tyr Cys Gln Gln Tyr Ser Gly Tyr Pro Ile Thr Phe Gly Ala Gly
                245                 250                 255
Thr Lys Val Glu Val Lys Arg Ser Asp Pro Ala Glu Pro Lys Ser Pro
                260                 265                 270
Asp Lys Thr His Thr Cys Pro Pro Cys Pro Ala Pro Glu Leu Leu Gly
                275                 280                 285
Gly Pro Ser Val Phe Leu Phe Pro Pro Lys Pro Lys Asp Thr Leu Met
                290                 295                 300
Ile Ser Arg Thr Pro Glu Val Thr Cys Val Val Val Asp Val Ser His
305                 310                 315                 320
Glu Asp Pro Glu Val Lys Phe Asn Trp Tyr Val Asp Gly Val Glu Val
                325                 330                 335
His Asn Ala Lys Thr Lys Pro Arg Glu Glu Gln Tyr Asn Ser Thr Tyr
                340                 345                 350
Arg Val Val Ser Val Leu Thr Val Leu His Gln Asp Trp Leu Asn Gly
                355                 360                 365
Lys Glu Tyr Lys Cys Lys Val Ser Asn Lys Ala Leu Pro Ala Pro Ile
                370                 375                 380
Glu Lys Thr Ile Ser Lys Ala Lys Gly Gln Pro Arg Glu Pro Gln Val
385                 390                 395                 400
Tyr Thr Leu Pro Pro Ser Arg Asp Glu Leu Thr Lys Asn Gln Val Ser
                405                 410                 415
Leu Thr Cys Leu Val Lys Gly Phe Tyr Pro Ser Asp Ile Ala Val Glu
                420                 425                 430
Trp Glu Ser Asn Gly Gln Pro Glu Asn Asn Tyr Lys Thr Thr Pro Pro
                435                 440                 445
```

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Lys Asp Pro Lys Phe Trp Val Leu Val Val Val Gly Gly
            500                 505                 510

Val Leu Ala Cys Tyr Ser Leu Leu Val Thr Val Ala Phe Ile Ile Phe
        515                 520                 525

Trp Val Arg Ser Lys Arg Ser Arg Leu Leu His Ser Asp Tyr Met Asn
    530                 535                 540

Met Thr Pro Arg Arg Pro Gly Pro Thr Arg Lys His Tyr Gln Pro Tyr
545                 550                 555                 560

Ala Pro Pro Arg Asp Phe Ala Ala Tyr Arg Ser Arg Asp Gln Arg Leu
                565                 570                 575

Pro Pro Asp Ala His Lys Pro Pro Gly Gly Ser Phe Arg Thr Pro
            580                 585                 590

Ile Gln Glu Glu Gln Ala Asp Ala His Ser Thr Leu Ala Lys Ile Arg
        595                 600                 605

Val Lys Phe Ser Arg Ser Ala Asp Ala Pro Ala Tyr Gln Gln Gly Gln
    610                 615                 620

Asn Gln Leu Tyr Asn Glu Leu Asn Leu Gly Arg Arg Glu Glu Tyr Asp
625                 630                 635                 640

Val Leu Asp Lys Arg Arg Gly Arg Asp Pro Glu Met Gly Gly Lys Pro
                645                 650                 655

Arg Arg Lys Asn Pro Gln Glu Gly Leu Tyr Asn Glu Leu Gln Lys Asp
            660                 665                 670

Lys Met Ala Glu Ala Tyr Ser Glu Ile Gly Met Lys Gly Glu Arg Arg
        675                 680                 685

Arg Gly Lys Gly His Asp Gly Leu Tyr Gln Gly Leu Ser Thr Ala Thr
    690                 695                 700

Lys Asp Thr Tyr Asp Ala Leu His Met Gln Ala Leu Pro Pro Arg
705                 710                 715

<210> SEQ ID NO 27
<211> LENGTH: 718
<212> TYPE: PRT
<213> ORGANISM: Artificial Sequence
<220> FEATURE:
<223> OTHER INFORMATION: anti-GD2 CAR, huKM666-HCH2CH3-CD28OXZ

<400> SEQUENCE: 27

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Gln Thr Leu Ser Ile Thr Cys Thr Val Ser Gly Phe Ser
        35                  40                  45

Leu Ala Ser Tyr Asn Ile His Trp Val Arg Gln Pro Pro Gly Lys Gly
    50                  55                  60

Leu Glu Trp Leu Gly Val Ile Trp Ala Gly Gly Ser Thr Asn Tyr Asn
65                  70                  75                  80

Ser Ala Leu Met Ser Arg Leu Thr Ile Ser Lys Asp Asn Ser Lys Asn
                85                  90                  95

-continued

```
Gln Val Phe Leu Lys Met Ser Ser Leu Thr Ala Ala Asp Thr Ala Val
                100                 105                 110
Tyr Tyr Cys Ala Lys Arg Ser Asp Asp Tyr Ser Trp Phe Ala Tyr Trp
            115                 120                 125
Gly Gln Gly Thr Leu Val Thr Val Ser Ser Gly Gly Gly Gly Ser Gly
        130                 135                 140
Gly Gly Ser Gly Gly Gly Gly Ser Glu Asn Gln Met Thr Gln Ser
145                 150                 155                 160
Pro Ser Ser Leu Ser Ala Ser Val Gly Asp Arg Val Thr Met Thr Cys
                165                 170                 175
Arg Ala Ser Ser Ser Val Ser Ser Ser Tyr Leu His Trp Tyr Gln Gln
            180                 185                 190
Lys Ser Gly Lys Ala Pro Lys Val Trp Ile Tyr Ser Thr Ser Asn Leu
        195                 200                 205
Ala Ser Gly Val Pro Ser Arg Phe Ser Gly Ser Gly Ser Gly Thr Asp
210                 215                 220
Tyr Thr Leu Thr Ile Ser Ser Leu Gln Pro Glu Asp Phe Ala Thr Tyr
225                 230                 235                 240
Tyr Cys Gln Gln Tyr Ser Gly Tyr Pro Ile Thr Phe Gly Gln Gly Thr
            245                 250                 255
Lys Val Glu Ile Lys Arg Ser Asp Pro Ala Glu Pro Lys Ser Pro Asp
        260                 265                 270
Lys Thr His Thr Cys Pro Pro Cys Pro Ala Pro Glu Leu Leu Gly Gly
            275                 280                 285
Pro Ser Val Phe Leu Phe Pro Pro Lys Pro Lys Asp Thr Leu Met Ile
        290                 295                 300
Ser Arg Thr Pro Glu Val Thr Cys Val Val Val Asp Val Ser His Glu
305                 310                 315                 320
Asp Pro Glu Val Lys Phe Asn Trp Tyr Val Asp Gly Val Glu Val His
                325                 330                 335
Asn Ala Lys Thr Lys Pro Arg Glu Glu Gln Tyr Asn Ser Thr Tyr Arg
            340                 345                 350
Val Val Ser Val Leu Thr Val Leu His Gln Asp Trp Leu Asn Gly Lys
        355                 360                 365
Glu Tyr Lys Cys Lys Val Ser Asn Lys Ala Leu Pro Ala Pro Ile Glu
    370                 375                 380
Lys Thr Ile Ser Lys Ala Lys Gly Gln Pro Arg Glu Pro Gln Val Tyr
385                 390                 395                 400
Thr Leu Pro Pro Ser Arg Asp Glu Leu Thr Lys Asn Gln Val Ser Leu
                405                 410                 415
Thr Cys Leu Val Lys Gly Phe Tyr Pro Ser Asp Ile Ala Val Glu Trp
            420                 425                 430
Glu Ser Asn Gly Gln Pro Glu Asn Asn Tyr Lys Thr Thr Pro Pro Val
        435                 440                 445
Leu Asp Ser Asp Gly Ser Phe Phe Leu Tyr Ser Lys Leu Thr Val Asp
    450                 455                 460
Lys Ser Arg Trp Gln Gln Gly Asn Val Phe Ser Cys Ser Val Met His
465                 470                 475                 480
Glu Ala Leu His Asn His Tyr Thr Gln Lys Ser Leu Ser Leu Ser Pro
                485                 490                 495
Gly Lys Lys Asp Pro Lys Phe Trp Val Leu Val Val Val Gly Gly Val
            500                 505                 510
```

```
Leu Ala Cys Tyr Ser Leu Leu Val Thr Val Ala Phe Ile Ile Phe Trp
            515                 520                 525

Val Arg Ser Lys Arg Ser Arg Leu Leu His Ser Asp Tyr Met Asn Met
    530                 535                 540

Thr Pro Arg Arg Pro Gly Pro Thr Arg Lys His Tyr Gln Pro Tyr Ala
545                 550                 555                 560

Pro Pro Arg Asp Phe Ala Ala Tyr Arg Ser Arg Asp Gln Arg Leu Pro
                565                 570                 575

Pro Asp Ala His Lys Pro Pro Gly Gly Ser Phe Arg Thr Pro Ile
                580                 585                 590

Gln Glu Glu Gln Ala Asp Ala His Ser Thr Leu Ala Lys Ile Arg Val
            595                 600                 605

Lys Phe Ser Arg Ser Ala Asp Ala Pro Ala Tyr Gln Gln Gly Gln Asn
    610                 615                 620

Gln Leu Tyr Asn Glu Leu Asn Leu Gly Arg Arg Glu Glu Tyr Asp Val
625                 630                 635                 640

Leu Asp Lys Arg Arg Gly Arg Asp Pro Glu Met Gly Gly Lys Pro Arg
                645                 650                 655

Arg Lys Asn Pro Gln Glu Gly Leu Tyr Asn Glu Leu Gln Lys Asp Lys
                660                 665                 670

Met Ala Glu Ala Tyr Ser Glu Ile Gly Met Lys Gly Glu Arg Arg Arg
            675                 680                 685

Gly Lys Gly His Asp Gly Leu Tyr Gln Gly Leu Ser Thr Ala Thr Lys
    690                 695                 700

Asp Thr Tyr Asp Ala Leu His Met Gln Ala Leu Pro Pro Arg
705                 710                 715

<210> SEQ ID NO 28
<211> LENGTH: 717
<212> TYPE: PRT
<213> ORGANISM: Artificial Sequence
<220> FEATURE:
<223> OTHER INFORMATION: anti-GD2 CAR, huKM666-HCH2CH3pvaa-CD28OXZ

<400> SEQUENCE: 28

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Gln Thr Leu Ser Ile Thr Cys Thr Val Ser Gly Phe Ser
        35                  40                  45

Leu Ala Ser Tyr Asn Ile His Trp Val Arg Gln Pro Pro Gly Lys Gly
    50                  55                  60

Leu Glu Trp Leu Gly Val Ile Trp Ala Gly Gly Ser Thr Asn Tyr Asn
65                  70                  75                  80

Ser Ala Leu Met Ser Arg Leu Thr Ile Ser Lys Asp Asn Ser Lys Asn
                85                  90                  95

Gln Val Phe Leu Lys Met Ser Ser Leu Thr Ala Ala Asp Thr Ala Val
            100                 105                 110

Tyr Tyr Cys Ala Lys Arg Ser Asp Asp Tyr Ser Trp Phe Ala Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Glu Asn Gln Met Thr Gln Ser
145                 150                 155                 160
```

```
Pro Ser Ser Leu Ser Ala Ser Val Gly Asp Arg Val Thr Met Thr Cys
            165                 170                 175
Arg Ala Ser Ser Val Ser Ser Ser Tyr Leu His Trp Tyr Gln Gln
        180                 185                 190
Lys Ser Gly Lys Ala Pro Lys Val Trp Ile Tyr Ser Thr Ser Asn Leu
        195                 200                 205
Ala Ser Gly Val Pro Ser Arg Phe Ser Gly Ser Gly Ser Gly Thr Asp
    210                 215                 220
Tyr Thr Leu Thr Ile Ser Ser Leu Gln Pro Glu Asp Phe Ala Thr Tyr
225                 230                 235                 240
Tyr Cys Gln Gln Tyr Ser Gly Tyr Pro Ile Thr Phe Gly Gln Gly Thr
                245                 250                 255
Lys Val Glu Ile Lys Arg Ser Asp Pro Ala Glu Pro Lys Ser Pro Asp
            260                 265                 270
Lys Thr His Thr Cys Pro Pro Cys Pro Ala Pro Val Ala Gly Pro
        275                 280                 285
Ser Val Phe Leu Phe Pro Pro Lys Pro Lys Asp Thr Leu Met Ile Ala
    290                 295                 300
Arg Thr Pro Glu Val Thr Cys Val Val Val Asp Val Ser His Glu Asp
305                 310                 315                 320
Pro Glu Val Lys Phe Asn Trp Tyr Val Asp Gly Val Glu Val His Asn
                325                 330                 335
Ala Lys Thr Lys Pro Arg Glu Glu Gln Tyr Asn Ser Thr Tyr Arg Val
            340                 345                 350
Val Ser Val Leu Thr Val Leu His Gln Asp Trp Leu Asn Gly Lys Glu
    355                 360                 365
Tyr Lys Cys Lys Val Ser Asn Lys Ala Leu Pro Ala Pro Ile Glu Lys
370                 375                 380
Thr Ile Ser Lys Ala Lys Gly Gln Pro Arg Glu Pro Gln Val Tyr Thr
385                 390                 395                 400
Leu Pro Pro Ser Arg Asp Glu Leu Thr Lys Asn Gln Val Ser Leu Thr
                405                 410                 415
Cys Leu Val Lys Gly Phe Tyr Pro Ser Asp Ile Ala Val Glu Trp Glu
            420                 425                 430
Ser Asn Gly Gln Pro Glu Asn Asn Tyr Lys Thr Thr Pro Pro Val Leu
    435                 440                 445
Asp Ser Asp Gly Ser Phe Phe Leu Tyr Ser Lys Leu Thr Val Asp Lys
450                 455                 460
Ser Arg Trp Gln Gln Gly Asn Val Phe Ser Cys Ser Val Met His Glu
465                 470                 475                 480
Ala Leu His Asn His Tyr Thr Gln Lys Ser Leu Ser Leu Ser Pro Gly
                485                 490                 495
Lys Lys Asp Pro Lys Phe Trp Val Leu Val Val Val Gly Gly Val Leu
            500                 505                 510
Ala Cys Tyr Ser Leu Leu Val Thr Val Ala Phe Ile Ile Phe Trp Val
    515                 520                 525
Arg Ser Lys Arg Ser Arg Leu Leu His Ser Asp Tyr Met Asn Met Thr
530                 535                 540
Pro Arg Arg Pro Gly Pro Thr Arg Lys His Tyr Gln Pro Tyr Ala Pro
545                 550                 555                 560
Pro Arg Asp Phe Ala Ala Tyr Arg Ser Arg Asp Gln Arg Leu Pro Pro
                565                 570                 575
Asp Ala His Lys Pro Pro Gly Gly Gly Ser Phe Arg Thr Pro Ile Gln
```

```
                    580                 585                 590
Glu Glu Gln Ala Asp Ala His Ser Thr Leu Ala Lys Ile Arg Val Lys
                595                 600                 605

Phe Ser Arg Ser Ala Asp Ala Pro Ala Tyr Gln Gln Gly Gln Asn Gln
            610                 615                 620

Leu Tyr Asn Glu Leu Asn Leu Gly Arg Arg Glu Glu Tyr Asp Val Leu
625                 630                 635                 640

Asp Lys Arg Arg Gly Arg Asp Pro Glu Met Gly Gly Lys Pro Arg Arg
                645                 650                 655

Lys Asn Pro Gln Glu Gly Leu Tyr Asn Glu Leu Gln Lys Asp Lys Met
            660                 665                 670

Ala Glu Ala Tyr Ser Glu Ile Gly Met Lys Gly Glu Arg Arg Arg Gly
                675                 680                 685

Lys Gly His Asp Gly Leu Tyr Gln Gly Leu Ser Thr Ala Thr Lys Asp
            690                 695                 700

Thr Tyr Asp Ala Leu His Met Gln Ala Leu Pro Pro Arg
705                 710                 715

<210> SEQ ID NO 29
<211> LENGTH: 527
<212> TYPE: PRT
<213> ORGANISM: Artificial Sequence
<220> FEATURE:
<223> OTHER INFORMATION: anti-GD2 CAR, huKM666-HSTK-CD28OXZ

<400> SEQUENCE: 29

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Gln Thr Leu Ser Ile Thr Cys Thr Val Ser Gly Phe Ser
        35                  40                  45

Leu Ala Ser Tyr Asn Ile His Trp Val Arg Gln Pro Pro Gly Lys Gly
    50                  55                  60

Leu Glu Trp Leu Gly Val Ile Trp Ala Gly Gly Ser Thr Asn Tyr Asn
65                  70                  75                  80

Ser Ala Leu Met Ser Arg Leu Thr Ile Ser Lys Asp Asn Ser Lys Asn
                85                  90                  95

Gln Val Phe Leu Lys Met Ser Ser Leu Thr Ala Ala Asp Thr Ala Val
            100                 105                 110

Tyr Tyr Cys Ala Lys Arg Ser Asp Asp Tyr Ser Trp Phe Ala Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Glu Asn Gln Met Thr Gln Ser
145                 150                 155                 160

Pro Ser Ser Leu Ser Ala Ser Val Gly Asp Arg Val Thr Met Thr Cys
                165                 170                 175

Arg Ala Ser Ser Ser Val Ser Ser Ser Tyr Leu His Trp Tyr Gln Gln
            180                 185                 190

Lys Ser Gly Lys Ala Pro Lys Val Trp Ile Tyr Ser Thr Ser Asn Leu
        195                 200                 205

Ala Ser Gly Val Pro Ser Arg Phe Ser Gly Ser Gly Ser Gly Thr Asp
    210                 215                 220

Tyr Thr Leu Thr Ile Ser Ser Leu Gln Pro Glu Asp Phe Ala Thr Tyr
```

```
            225                 230                 235                 240

Tyr Cys Gln Gln Tyr Ser Gly Tyr Pro Ile Thr Phe Gly Gln Gly Thr
                245                 250                 255

Lys Val Glu Ile Lys Arg Ser Asp Pro Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Phe Trp Val Leu Val Val Val Gly Gly
305                 310                 315                 320

Val Leu Ala Cys Tyr Ser Leu Leu Val Thr Val Ala Phe Ile Ile Phe
                325                 330                 335

Trp Val Arg Ser Lys Arg Ser Arg Leu Leu His Ser Asp Tyr Met Asn
            340                 345                 350

Met Thr Pro Arg Arg Pro Gly Pro Thr Arg Lys His Tyr Gln Pro Tyr
        355                 360                 365

Ala Pro Pro Arg Asp Phe Ala Ala Tyr Arg Ser Arg Asp Gln Arg Leu
    370                 375                 380

Pro Pro Asp Ala His Lys Pro Pro Gly Gly Gly Ser Phe Arg Thr Pro
385                 390                 395                 400

Ile Gln Glu Glu Gln Ala Asp Ala His Ser Thr Leu Ala Lys Ile Arg
                405                 410                 415

Val Lys Phe Ser Arg Ser Ala Asp Ala Pro Ala Tyr Gln Gln Gly Gln
            420                 425                 430

Asn Gln Leu Tyr Asn Glu Leu Asn Leu Gly Arg Arg Glu Glu Tyr Asp
        435                 440                 445

Val Leu Asp Lys Arg Arg Gly Arg Asp Pro Glu Met Gly Gly Lys Pro
    450                 455                 460

Arg Arg Lys Asn Pro Gln Glu Gly Leu Tyr Asn Glu Leu Gln Lys Asp
465                 470                 475                 480

Lys Met Ala Glu Ala Tyr Ser Glu Ile Gly Met Lys Gly Glu Arg Arg
                485                 490                 495

Arg Gly Lys Gly His Asp Gly Leu Tyr Gln Gly Leu Ser Thr Ala Thr
            500                 505                 510

Lys Asp Thr Tyr Asp Ala Leu His Met Gln Ala Leu Pro Pro Arg
        515                 520                 525

<210> SEQ ID NO 30
<211> LENGTH: 527
<212> TYPE: PRT
<213> ORGANISM: Artificial Sequence
<220> FEATURE:
<223> OTHER INFORMATION: anti-GD2 CAR, huKM666-STK-CD28XOXZ

<400> SEQUENCE: 30

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Gln Thr Leu Ser Ile Thr Cys Thr Val Ser Gly Phe Ser
        35                  40                  45

Leu Ala Ser Tyr Asn Ile His Trp Val Arg Gln Pro Pro Gly Lys Gly
    50                  55                  60

Leu Glu Trp Leu Gly Val Ile Trp Ala Gly Gly Ser Thr Asn Tyr Asn
```

```
                65                  70                  75                  80
Ser Ala Leu Met Ser Arg Leu Thr Ile Ser Lys Asp Asn Ser Lys Asn
                        85                  90                  95
Gln Val Phe Leu Lys Met Ser Ser Leu Thr Ala Ala Asp Thr Ala Val
                        100                 105                 110
Tyr Tyr Cys Ala Lys Arg Ser Asp Asp Tyr Ser Trp Phe Ala Tyr Trp
                        115                 120                 125
Gly Gln Gly Thr Leu Val Thr Val Ser Ser Gly Gly Gly Gly Ser Gly
                130                 135                 140
Gly Gly Gly Ser Gly Gly Gly Ser Glu Asn Gln Met Thr Gln Ser
145                 150                 155                 160
Pro Ser Ser Leu Ser Ala Ser Val Gly Asp Arg Val Thr Met Thr Cys
                        165                 170                 175
Arg Ala Ser Ser Ser Val Ser Ser Ser Tyr Leu His Trp Tyr Gln Gln
                        180                 185                 190
Lys Ser Gly Lys Ala Pro Lys Val Trp Ile Tyr Ser Thr Ser Asn Leu
                        195                 200                 205
Ala Ser Gly Val Pro Ser Arg Phe Ser Gly Ser Gly Ser Gly Thr Asp
                210                 215                 220
Tyr Thr Leu Thr Ile Ser Ser Leu Gln Pro Glu Asp Phe Ala Thr Tyr
225                 230                 235                 240
Tyr Cys Gln Gln Tyr Ser Gly Tyr Pro Ile Thr Phe Gly Gln Gly Thr
                        245                 250                 255
Lys Val Glu Ile Lys Arg Ser Asp Pro Thr Thr Thr Pro Ala Pro Arg
                        260                 265                 270
Pro Pro Thr Pro Ala Pro Thr Ile Ala Ser Gln Pro Leu Ser Leu Arg
                        275                 280                 285
Pro Glu Ala Cys Arg Pro Ala Ala Gly Gly Ala Val His Thr Arg Gly
                        290                 295                 300
Leu Asp Phe Ala Cys Asp Ile Phe Trp Val Leu Val Val Val Gly Gly
305                 310                 315                 320
Val Leu Ala Cys Tyr Ser Leu Leu Val Thr Val Ala Phe Ile Ile Phe
                        325                 330                 335
Trp Val Arg Ser Lys Arg Ser Arg Leu Leu His Ser Asp Tyr Met Asn
                        340                 345                 350
Met Thr Pro Arg Arg Pro Gly Pro Thr Arg Lys His Tyr Gln Pro Tyr
                        355                 360                 365
Ala Pro Pro Arg Asp Phe Ala Ala Tyr Arg Ser Arg Asp Gln Arg Leu
                        370                 375                 380
Pro Pro Asp Ala His Lys Pro Pro Gly Gly Gly Ser Phe Arg Thr Pro
385                 390                 395                 400
Ile Gln Glu Glu Gln Ala Asp Ala His Ser Thr Leu Ala Lys Ile Arg
                        405                 410                 415
Val Lys Phe Ser Arg Ser Ala Asp Ala Pro Ala Tyr Gln Gln Gly Gln
                        420                 425                 430
Asn Gln Leu Tyr Asn Glu Leu Asn Leu Gly Arg Arg Glu Glu Tyr Asp
                        435                 440                 445
Val Leu Asp Lys Arg Arg Gly Arg Asp Pro Glu Met Gly Gly Lys Pro
                450                 455                 460
Arg Arg Lys Asn Pro Gln Glu Gly Leu Tyr Asn Glu Leu Gln Lys Asp
465                 470                 475                 480
Lys Met Ala Glu Ala Tyr Ser Glu Ile Gly Met Lys Gly Glu Arg Arg
                        485                 490                 495
```

```
Arg Gly Lys Gly His Asp Gly Leu Tyr Gln Gly Leu Ser Thr Ala Thr
            500                 505                 510

Lys Asp Thr Tyr Asp Ala Leu His Met Gln Ala Leu Pro Pro Arg
            515                 520                 525

<210> SEQ ID NO 31
<211> LENGTH: 501
<212> TYPE: PRT
<213> ORGANISM: Artificial Sequence
<220> FEATURE:
<223> OTHER INFORMATION: anti-GD2 CAR, huKM666-HNG-CD28OXZ

<400> SEQUENCE: 31

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Gln Thr Leu Ser Ile Thr Cys Thr Val Ser Gly Phe Ser
        35                  40                  45

Leu Ala Ser Tyr Asn Ile His Trp Val Arg Gln Pro Pro Gly Lys Gly
    50                  55                  60

Leu Glu Trp Leu Gly Val Ile Trp Ala Gly Gly Ser Thr Asn Tyr Asn
65                  70                  75                  80

Ser Ala Leu Met Ser Arg Leu Thr Ile Ser Lys Asp Asn Ser Lys Asn
                85                  90                  95

Gln Val Phe Leu Lys Met Ser Ser Leu Thr Ala Ala Asp Thr Ala Val
            100                 105                 110

Tyr Tyr Cys Ala Lys Arg Ser Asp Asp Tyr Ser Trp Phe Ala Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Ser Glu Asn Gln Met Thr Gln Ser
145                 150                 155                 160

Pro Ser Ser Leu Ser Ala Ser Val Gly Asp Arg Val Thr Met Thr Cys
                165                 170                 175

Arg Ala Ser Ser Ser Val Ser Ser Ser Tyr Leu His Trp Tyr Gln Gln
            180                 185                 190

Lys Ser Gly Lys Ala Pro Lys Val Trp Ile Tyr Ser Thr Ser Asn Leu
        195                 200                 205

Ala Ser Gly Val Pro Ser Arg Phe Ser Gly Ser Gly Ser Gly Thr Asp
    210                 215                 220

Tyr Thr Leu Thr Ile Ser Ser Leu Gln Pro Glu Asp Phe Ala Thr Tyr
225                 230                 235                 240

Tyr Cys Gln Gln Tyr Ser Gly Tyr Pro Ile Thr Phe Gly Gln Gly Thr
                245                 250                 255

Lys Val Glu Ile Lys Arg Ser Asp Pro Ala Glu Pro Lys Ser Pro Asp
            260                 265                 270

Lys Thr His Thr Cys Pro Pro Cys Pro Lys Asp Pro Lys Phe Trp Val
        275                 280                 285

Leu Val Val Val Gly Gly Val Leu Ala Cys Tyr Ser Leu Leu Val Thr
    290                 295                 300

Val Ala Phe Ile Ile Phe Trp Val Arg Ser Lys Arg Ser Arg Leu Leu
305                 310                 315                 320

His Ser Asp Tyr Met Asn Met Thr Pro Arg Arg Pro Gly Pro Thr Arg
                325                 330                 335
```

```
Lys His Tyr Gln Pro Tyr Ala Pro Pro Arg Asp Phe Ala Ala Tyr Arg
                340                 345                 350

Ser Arg Asp Gln Arg Leu Pro Pro Asp Ala His Lys Pro Pro Gly Gly
            355                 360                 365

Gly Ser Phe Arg Thr Pro Ile Gln Glu Glu Ala Asp Ala His Ser
    370                 375                 380

Thr Leu Ala Lys Ile Arg Val Lys Phe Ser Arg Ser Ala Asp Ala Pro
385                 390                 395                 400

Ala Tyr Gln Gln Gly Gln Asn Gln Leu Tyr Asn Glu Leu Asn Leu Gly
                405                 410                 415

Arg Arg Glu Glu Tyr Asp Val Leu Asp Lys Arg Arg Gly Arg Asp Pro
            420                 425                 430

Glu Met Gly Gly Lys Pro Arg Arg Lys Asn Pro Gln Glu Gly Leu Tyr
        435                 440                 445

Asn Glu Leu Gln Lys Asp Lys Met Ala Glu Ala Tyr Ser Glu Ile Gly
                450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495

Ala Leu Pro Pro Arg
            500

<210> SEQ ID NO 32
<211> LENGTH: 642
<212> TYPE: PRT
<213> ORGANISM: Artificial Sequence
<220> FEATURE:
<223> OTHER INFORMATION: anti-GD2 CAR, huKM666-HCH2CH3pvaa-CD28tmZ

<400> SEQUENCE: 32

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Gln Thr Leu Ser Ile Thr Cys Thr Val Ser Gly Phe Ser
        35                  40                  45

Leu Ala Ser Tyr Asn Ile His Trp Val Arg Gln Pro Pro Gly Lys Gly
    50                  55                  60

Leu Glu Trp Leu Gly Val Ile Trp Ala Gly Gly Ser Thr Asn Tyr Asn
65                  70                  75                  80

Ser Ala Leu Met Ser Arg Leu Thr Ile Ser Lys Asp Asn Ser Lys Asn
                85                  90                  95

Gln Val Phe Leu Lys Met Ser Ser Leu Thr Ala Ala Asp Thr Ala Val
            100                 105                 110

Tyr Tyr Cys Ala Lys Arg Ser Asp Asp Tyr Ser Trp Phe Ala Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Glu Asn Gln Met Thr Gln Ser
145                 150                 155                 160

Pro Ser Ser Leu Ser Ala Ser Val Gly Asp Arg Val Thr Met Thr Cys
                165                 170                 175

Arg Ala Ser Ser Ser Val Ser Ser Ser Tyr Leu His Trp Tyr Gln Gln
            180                 185                 190
```

```
Lys Ser Gly Lys Ala Pro Lys Val Trp Ile Tyr Ser Thr Ser Asn Leu
            195                 200                 205

Ala Ser Gly Val Pro Ser Arg Phe Ser Gly Ser Gly Ser Gly Thr Asp
            210                 215                 220

Tyr Thr Leu Thr Ile Ser Ser Leu Gln Pro Glu Asp Phe Ala Thr Tyr
225                 230                 235                 240

Tyr Cys Gln Gln Tyr Ser Gly Tyr Pro Ile Thr Phe Gly Gln Gly Thr
                245                 250                 255

Lys Val Glu Ile Lys Arg Ser Asp Pro Ala Glu Pro Lys Ser Pro Asp
            260                 265                 270

Lys Thr His Thr Cys Pro Pro Cys Pro Ala Pro Pro Val Ala Gly Pro
            275                 280                 285

Ser Val Phe Leu Phe Pro Pro Lys Pro Lys Asp Thr Leu Met Ile Ala
            290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Lys Leu Thr Val Asp Lys
            450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys Lys Asp Pro Lys Phe Trp Val Leu Val Val Val Gly Gly Val Leu
            500                 505                 510

Ala Cys Tyr Ser Leu Leu Val Thr Val Ala Phe Ile Ile Phe Trp Val
            515                 520                 525

Arg Ser Arg Val Lys Phe Ser Arg Ser Ala Asp Ala Pro Ala Tyr Gln
530                 535                 540

Gln Gly Gln Asn Gln Leu Tyr Asn Glu Leu Asn Leu Gly Arg Arg Glu
545                 550                 555                 560

Glu Tyr Asp Val Leu Asp Lys Arg Arg Gly Arg Asp Pro Glu Met Gly
                565                 570                 575

Gly Lys Pro Arg Arg Lys Asn Pro Gln Glu Gly Leu Tyr Asn Glu Leu
            580                 585                 590

Gln Lys Asp Lys Met Ala Glu Ala Tyr Ser Glu Ile Gly Met Lys Gly
            595                 600                 605
```

-continued

Glu Arg Arg Arg Gly Lys Gly His Asp Gly Leu Tyr Gln Gly Leu Ser
610             615                 620

Thr Ala Thr Lys Asp Thr Tyr Asp Ala Leu His Met Gln Ala Leu Pro
625             630                 635                 640

Pro Arg

<210> SEQ ID NO 33
<211> LENGTH: 681
<212> TYPE: PRT
<213> ORGANISM: Artificial Sequence
<220> FEATURE:
<223> OTHER INFORMATION: anti-GD2 CAR, huMK666-HCH2CH3pvaa-CD28Z

<400> SEQUENCE: 33

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
                20                  25                  30

Lys Pro Ser Gln Thr Leu Ser Ile Thr Cys Thr Val Ser Gly Phe Ser
            35                  40                  45

Leu Ala Ser Tyr Asn Ile His Trp Val Arg Gln Pro Pro Gly Lys Gly
        50                  55                  60

Leu Glu Trp Leu Gly Val Ile Trp Ala Gly Gly Ser Thr Asn Tyr Asn
65                  70                  75                  80

Ser Ala Leu Met Ser Arg Leu Thr Ile Ser Lys Asp Asn Ser Lys Asn
                85                  90                  95

Gln Val Phe Leu Lys Met Ser Ser Leu Thr Ala Ala Asp Thr Ala Val
            100                 105                 110

Tyr Tyr Cys Ala Lys Arg Ser Asp Asp Tyr Ser Trp Phe Ala Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Glu Asn Gln Met Thr Gln Ser
145                 150                 155                 160

Pro Ser Ser Leu Ser Ala Ser Val Gly Asp Arg Val Thr Met Thr Cys
                165                 170                 175

Arg Ala Ser Ser Ser Val Ser Ser Ser Tyr Leu His Trp Tyr Gln Gln
            180                 185                 190

Lys Ser Gly Lys Ala Pro Lys Val Trp Ile Tyr Ser Thr Ser Asn Leu
        195                 200                 205

Ala Ser Gly Val Pro Ser Arg Phe Ser Gly Ser Gly Ser Gly Thr Asp
    210                 215                 220

Tyr Thr Leu Thr Ile Ser Ser Leu Gln Pro Glu Asp Phe Ala Thr Tyr
225                 230                 235                 240

Tyr Cys Gln Gln Tyr Ser Gly Tyr Pro Ile Thr Phe Gly Gln Gly Thr
                245                 250                 255

Lys Val Glu Ile Lys Arg Ser Asp Pro Ala Glu Pro Lys Ser Pro Asp
            260                 265                 270

Lys Thr His Thr Cys Pro Pro Cys Pro Ala Pro Val Ala Gly Pro
        275                 280                 285

Ser Val Phe Leu Phe Pro Pro Lys Pro Lys Asp Thr Leu Met Ile Ala
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn

```
            325                 330                 335
Ala Lys Thr Lys Pro Arg Glu Glu Gln Tyr Asn Ser Thr Tyr Arg Val
                340                 345                 350
Val Ser Val Leu Thr Val Leu His Gln Asp Trp Leu Asn Gly Lys Glu
            355                 360                 365
Tyr Lys Cys Lys Val Ser Asn Lys Ala Leu Pro Ala Pro Ile Glu Lys
        370                 375                 380
Thr Ile Ser Lys Ala Lys Gly Gln Pro Arg Glu Pro Gln Val Tyr Thr
385                 390                 395                 400
Leu Pro Pro Ser Arg Asp Glu Leu Thr Lys Asn Gln Val Ser Leu Thr
                405                 410                 415
Cys Leu Val Lys Gly Phe Tyr Pro Ser Asp Ile Ala Val Glu Trp Glu
            420                 425                 430
Ser Asn Gly Gln Pro Glu Asn Asn Tyr Lys Thr Thr Pro Pro Val Leu
        435                 440                 445
Asp Ser Asp Gly Ser Phe Phe Leu Tyr Ser Lys Leu Thr Val Asp Lys
    450                 455                 460
Ser Arg Trp Gln Gln Gly Asn Val Phe Ser Cys Ser Val Met His Glu
465                 470                 475                 480
Ala Leu His Asn His Tyr Thr Gln Lys Ser Leu Ser Leu Ser Pro Gly
                485                 490                 495
Lys Lys Asp Pro Lys Phe Trp Val Leu Val Val Val Gly Gly Val Leu
            500                 505                 510
Ala Cys Tyr Ser Leu Leu Val Thr Val Ala Phe Ile Ile Phe Trp Val
        515                 520                 525
Arg Ser Lys Arg Ser Arg Leu Leu His Ser Asp Tyr Met Asn Met Thr
    530                 535                 540
Pro Arg Arg Pro Gly Pro Thr Arg Lys His Tyr Gln Pro Tyr Ala Pro
545                 550                 555                 560
Pro Arg Asp Phe Ala Ala Tyr Arg Ser Arg Val Lys Phe Ser Arg Ser
                565                 570                 575
Ala Asp Ala Pro Ala Tyr Gln Gln Gly Gln Asn Gln Leu Tyr Asn Glu
            580                 585                 590
Leu Asn Leu Gly Arg Arg Glu Glu Tyr Asp Val Leu Asp Lys Arg Arg
        595                 600                 605
Gly Arg Asp Pro Glu Met Gly Gly Lys Pro Arg Arg Lys Asn Pro Gln
    610                 615                 620
Glu Gly Leu Tyr Asn Glu Leu Gln Lys Asp Lys Met Ala Glu Ala Tyr
625                 630                 635                 640
Ser Glu Ile Gly Met Lys Gly Glu Arg Arg Arg Gly Lys Gly His Asp
                645                 650                 655
Gly Leu Tyr Gln Gly Leu Ser Thr Ala Thr Lys Asp Thr Tyr Asp Ala
            660                 665                 670
Leu His Met Gln Ala Leu Pro Pro Arg
        675                 680

<210> SEQ ID NO 34
<211> LENGTH: 1103
<212> TYPE: PRT
<213> ORGANISM: Artificial Sequence
<220> FEATURE:
<223> OTHER INFORMATION: anti-GD2 CAR co-expressed with iCasp9 suicide
      gene

<400> SEQUENCE: 34
```

```
Met Leu Glu Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
                20                  25                  30

Leu Glu Asp Gly Lys Lys Val Asp Ser Ser Arg Asp Arg Asn Lys Pro
            35                  40                  45

Phe Lys Phe Met Leu Gly Lys Gln Glu Val Ile Arg Gly Trp Glu Glu
        50                  55                  60

Gly Val Ala Gln Met Ser Val Gly Gln Arg Ala Lys Leu Thr Ile Ser
65                  70                  75                  80

Pro Asp Tyr Ala Tyr Gly Ala Thr Gly His Pro Gly Ile Ile Pro Pro
                85                  90                  95

His Ala Thr Leu Val Phe Asp Val Glu Leu Leu Lys Leu Glu Ser Gly
            100                 105                 110

Gly Gly Ser Gly Val Asp Gly Phe Gly Asp Val Gly Ala Leu Glu Ser
        115                 120                 125

Leu Arg Gly Asn Ala Asp Leu Ala Tyr Ile Leu Ser Met Glu Pro Cys
    130                 135                 140

Gly His Cys Leu Ile Ile Asn Asn Val Asn Phe Cys Arg Glu Ser Gly
145                 150                 155                 160

Leu Arg Thr Arg Thr Gly Ser Asn Ile Asp Cys Glu Lys Leu Arg Arg
                165                 170                 175

Arg Phe Ser Ser Leu His Phe Met Val Glu Val Lys Gly Asp Leu Thr
            180                 185                 190

Ala Lys Lys Met Val Leu Ala Leu Leu Glu Leu Ala Gln Gln Asp His
        195                 200                 205

Gly Ala Leu Asp Cys Cys Val Val Ile Leu Ser His Gly Cys Gln
210                 215                 220

Ala Ser His Leu Gln Phe Pro Gly Ala Val Tyr Gly Thr Asp Gly Cys
225                 230                 235                 240

Pro Val Ser Val Glu Lys Ile Val Asn Ile Phe Asn Gly Thr Ser Cys
                245                 250                 255

Pro Ser Leu Gly Gly Lys Pro Lys Leu Phe Phe Ile Gln Ala Cys Gly
            260                 265                 270

Gly Glu Gln Lys Asp His Gly Phe Glu Val Ala Ser Thr Ser Pro Glu
        275                 280                 285

Asp Glu Ser Pro Gly Ser Asn Pro Glu Pro Asp Ala Thr Pro Phe Gln
    290                 295                 300

Glu Gly Leu Arg Thr Phe Asp Gln Leu Asp Ala Ile Ser Ser Leu Pro
305                 310                 315                 320

Thr Pro Ser Asp Ile Phe Val Ser Tyr Ser Thr Phe Pro Gly Phe Val
                325                 330                 335

Ser Trp Arg Asp Pro Lys Ser Gly Ser Trp Tyr Val Glu Thr Leu Asp
            340                 345                 350

Asp Ile Phe Glu Gln Trp Ala His Ser Glu Asp Leu Gln Ser Leu Leu
        355                 360                 365

Leu Arg Val Ala Asn Ala Val Ser Val Lys Gly Ile Tyr Lys Gln Met
    370                 375                 380

Pro Gly Cys Phe Asn Phe Leu Arg Lys Lys Leu Phe Phe Lys Thr Ser
385                 390                 395                 400

Ala Ser Arg Ala Glu Gly Arg Gly Ser Leu Leu Thr Cys Gly Asp Val
                405                 410                 415

Glu Glu Asn Pro Gly Pro Met Glu Thr Asp Thr Leu Leu Leu Trp Val
```

```
                420             425             430
Leu Leu Leu Trp Val Pro Gly Ser Thr Gly Gln Val Gln Leu Gln Glu
            435                 440                 445

Ser Gly Pro Gly Leu Val Lys Pro Ser Gln Thr Leu Ser Ile Thr Cys
            450                 455                 460

Thr Val Ser Gly Phe Ser Leu Ala Ser Tyr Asn Ile His Trp Val Arg
465                 470                 475                 480

Gln Pro Pro Gly Lys Gly Leu Glu Trp Leu Gly Val Ile Trp Ala Gly
            485                 490                 495

Gly Ser Thr Asn Tyr Asn Ser Ala Leu Met Ser Arg Leu Thr Ile Ser
            500                 505                 510

Lys Asp Asn Ser Lys Asn Gln Val Phe Leu Lys Met Ser Ser Leu Thr
            515                 520                 525

Ala Ala Asp Thr Ala Val Tyr Tyr Cys Ala Lys Arg Ser Asp Asp Tyr
            530                 535                 540

Ser Trp Phe Ala Tyr Trp Gly Gln Gly Thr Leu Val Thr Val Ser Ser
545                 550                 555                 560

Gly Gly Gly Gly Ser Gly Gly Gly Ser Gly Gly Gly Gly Ser Glu
            565                 570                 575

Asn Gln Met Thr Gln Ser Pro Ser Ser Leu Ser Ala Ser Val Gly Asp
            580                 585                 590

Arg Val Thr Met Thr Cys Arg Ala Ser Ser Ser Val Ser Ser Ser Tyr
            595                 600                 605

Leu His Trp Tyr Gln Gln Lys Ser Gly Lys Ala Pro Lys Val Trp Ile
            610                 615                 620

Tyr Ser Thr Ser Asn Leu Ala Ser Gly Val Pro Ser Arg Phe Ser Gly
625                 630                 635                 640

Ser Gly Ser Gly Thr Asp Tyr Thr Leu Thr Ile Ser Ser Leu Gln Pro
            645                 650                 655

Glu Asp Phe Ala Thr Tyr Tyr Cys Gln Gln Tyr Ser Gly Tyr Pro Ile
            660                 665                 670

Thr Phe Gly Gln Gly Thr Lys Val Glu Ile Lys Arg Ser Asp Pro Ala
            675                 680                 685

Glu Pro Lys Ser Pro Asp Lys Thr His Thr Cys Pro Pro Cys Pro Ala
            690                 695                 700

Pro Pro Val Ala Gly Pro Ser Val Phe Leu Phe Pro Pro Lys Pro Lys
705                 710                 715                 720

Asp Thr Leu Met Ile Ala Arg Thr Pro Glu Val Thr Cys Val Val Val
            725                 730                 735

Asp Val Ser His Glu Asp Pro Glu Val Lys Phe Asn Trp Tyr Val Asp
            740                 745                 750

Gly Val Glu Val His Asn Ala Lys Thr Lys Pro Arg Glu Glu Gln Tyr
            755                 760                 765

Asn Ser Thr Tyr Arg Val Val Ser Val Leu Thr Val Leu His Gln Asp
            770                 775                 780

Trp Leu Asn Gly Lys Glu Tyr Lys Cys Lys Val Ser Asn Lys Ala Leu
785                 790                 795                 800

Pro Ala Pro Ile Glu Lys Thr Ile Ser Lys Ala Lys Gly Gln Pro Arg
            805                 810                 815

Glu Pro Gln Val Tyr Thr Leu Pro Pro Ser Arg Asp Glu Leu Thr Lys
            820                 825                 830

Asn Gln Val Ser Leu Thr Cys Leu Val Lys Gly Phe Tyr Pro Ser Asp
            835                 840                 845
```

Ile Ala Val Glu Trp Glu Ser Asn Gly Gln Pro Glu Asn Asn Tyr Lys
850                 855                 860

Thr Thr Pro Pro Val Leu Asp Ser Asp Gly Ser Phe Phe Leu Tyr Ser
865                 870                 875                 880

Lys Leu Thr Val Asp Lys Ser Arg Trp Gln Gln Gly Asn Val Phe Ser
            885                 890                 895

Cys Ser Val Met His Glu Ala Leu His Asn His Tyr Thr Gln Lys Ser
            900                 905                 910

Leu Ser Leu Ser Pro Gly Lys Lys Asp Pro Lys Phe Trp Val Leu Val
            915                 920                 925

Val Val Gly Gly Val Leu Ala Cys Tyr Ser Leu Leu Val Thr Val Ala
930                 935                 940

Phe Ile Ile Phe Trp Val Arg Ser Lys Arg Ser Arg Leu Leu His Ser
945                 950                 955                 960

Asp Tyr Met Asn Met Thr Pro Arg Arg Pro Gly Pro Thr Arg Lys His
                965                 970                 975

Tyr Gln Pro Tyr Ala Pro Pro Arg Asp Phe Ala Ala Tyr Arg Ser Arg
            980                 985                 990

Val Lys Phe Ser Arg Ser Ala Asp Ala Pro Ala Tyr Gln Gln Gly Gln
            995                 1000                1005

Asn Gln Leu Tyr Asn Glu Leu Asn Leu Gly Arg Arg Glu Glu Tyr
        1010                1015                1020

Asp Val Leu Asp Lys Arg Arg Gly Arg Asp Pro Glu Met Gly Gly
        1025                1030                1035

Lys Pro Arg Arg Lys Asn Pro Gln Glu Gly Leu Tyr Asn Glu Leu
        1040                1045                1050

Gln Lys Asp Lys Met Ala Glu Ala Tyr Ser Glu Ile Gly Met Lys
        1055                1060                1065

Gly Glu Arg Arg Arg Gly Lys Gly His Asp Gly Leu Tyr Gln Gly
        1070                1075                1080

Leu Ser Thr Ala Thr Lys Asp Thr Tyr Asp Ala Leu His Met Gln
        1085                1090                1095

Ala Leu Pro Pro Arg
        1100

<210> SEQ ID NO 35
<211> LENGTH: 858
<212> TYPE: PRT
<213> ORGANISM: Artificial Sequence
<220> FEATURE:
<223> OTHER INFORMATION: anti-GD2 CAR co-expressed with RQR8 suicide
      gene

<400> SEQUENCE: 35

Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Gly Ser Pro Ala Pro Arg Pro
65                  70                  75                  80

Pro Thr Pro Ala Pro Thr Ile Ala Ser Gln Pro Leu Ser Leu Arg Pro

```
                        85                  90                  95
Glu Ala Cys Arg Pro Ala Ala Gly Gly Ala Val His Thr Arg Gly Leu
                100                 105                 110

Asp Phe Ala Cys Asp Ile Tyr Ile Trp Ala Pro Leu Ala Gly Thr Cys
            115                 120                 125

Gly Val Leu Leu Leu Ser Leu Val Ile Thr Leu Tyr Cys Asn His Arg
        130                 135                 140

Asn Arg Arg Arg Val Cys Lys Cys Pro Arg Pro Val Val Arg Ala Glu
145                 150                 155                 160

Gly Arg Gly Ser Leu Leu Thr Cys Gly Asp Val Glu Glu Asn Pro Gly
                165                 170                 175

Pro Met Glu Thr Asp Thr Leu Leu Leu Trp Val Leu Leu Leu Trp Val
                180                 185                 190

Pro Gly Ser Thr Gly Gln Val Gln Leu Gln Glu Ser Gly Pro Gly Leu
                195                 200                 205

Val Lys Pro Ser Gln Thr Leu Ser Ile Thr Cys Thr Val Ser Gly Phe
        210                 215                 220

Ser Leu Ala Ser Tyr Asn Ile His Trp Val Arg Gln Pro Pro Gly Lys
225                 230                 235                 240

Gly Leu Glu Trp Leu Gly Val Ile Trp Ala Gly Gly Ser Thr Asn Tyr
                245                 250                 255

Asn Ser Ala Leu Met Ser Arg Leu Thr Ile Ser Lys Asp Asn Ser Lys
                260                 265                 270

Asn Gln Val Phe Leu Lys Met Ser Ser Leu Thr Ala Ala Asp Thr Ala
            275                 280                 285

Val Tyr Tyr Cys Ala Lys Arg Ser Asp Asp Tyr Ser Trp Phe Ala Tyr
        290                 295                 300

Trp Gly Gln Gly Thr Leu Val Thr Val Ser Ser Gly Gly Gly Gly Ser
305                 310                 315                 320

Gly Gly Gly Gly Ser Gly Gly Gly Ser Glu Asn Gln Met Thr Gln
                325                 330                 335

Ser Pro Ser Ser Leu Ser Ala Ser Val Gly Asp Arg Val Thr Met Thr
                340                 345                 350

Cys Arg Ala Ser Ser Ser Val Ser Ser Ser Tyr Leu His Trp Tyr Gln
            355                 360                 365

Gln Lys Ser Gly Lys Ala Pro Lys Val Trp Ile Tyr Ser Thr Ser Asn
        370                 375                 380

Leu Ala Ser Gly Val Pro Ser Arg Phe Ser Gly Ser Gly Ser Gly Thr
385                 390                 395                 400

Asp Tyr Thr Leu Thr Ile Ser Ser Leu Gln Pro Glu Asp Phe Ala Thr
                405                 410                 415

Tyr Tyr Cys Gln Gln Tyr Ser Gly Tyr Pro Ile Thr Phe Gly Gln Gly
                420                 425                 430

Thr Lys Val Glu Ile Lys Arg Ser Asp Pro Ala Glu Pro Lys Ser Pro
            435                 440                 445

Asp Lys Thr His Thr Cys Pro Pro Cys Pro Ala Pro Pro Val Ala Gly
        450                 455                 460

Pro Ser Val Phe Leu Phe Pro Pro Lys Pro Lys Asp Thr Leu Met Ile
465                 470                 475                 480

Ala Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
                500                 505                 510
```

Asn Ala Lys Thr Lys Pro Arg Glu Glu Gln Tyr Asn Ser Thr Tyr Arg
            515                 520                 525

Val Val Ser Val Leu Thr Val Leu His Gln Asp Trp Leu Asn Gly Lys
        530                 535                 540

Glu Tyr Lys Cys Lys Val Ser Asn Lys Ala Leu Pro Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Ser Arg Asp Glu Leu Thr Lys Asn Gln Val Ser Leu
            580                 585                 590

Thr Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
    610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

Gly Lys Lys Asp Pro Lys Phe Trp Val Leu Val Val Val Gly Gly Val
        675                 680                 685

Leu Ala Cys Tyr Ser Leu Leu Val Thr Val Ala Phe Ile Ile Phe Trp
    690                 695                 700

Val Arg Ser Lys Arg Ser Arg Leu Leu His Ser Asp Tyr Met Asn Met
705                 710                 715                 720

Thr Pro Arg Arg Pro Gly Pro Thr Arg Lys His Tyr Gln Pro Tyr Ala
                725                 730                 735

Pro Pro Arg Asp Phe Ala Ala Tyr Arg Ser Arg Val Lys Phe Ser Arg
            740                 745                 750

Ser Ala Asp Ala Pro Ala Tyr Gln Gln Gly Gln Asn Gln Leu Tyr Asn
        755                 760                 765

Glu Leu Asn Leu Gly Arg Arg Glu Glu Tyr Asp Val Leu Asp Lys Arg
    770                 775                 780

Arg Gly Arg Asp Pro Glu Met Gly Gly Lys Pro Arg Arg Lys Asn Pro
785                 790                 795                 800

Gln Glu Gly Leu Tyr Asn Glu Leu Gln Lys Asp Lys Met Ala Glu Ala
                805                 810                 815

Tyr Ser Glu Ile Gly Met Lys Gly Glu Arg Arg Arg Gly Lys Gly His
            820                 825                 830

Asp Gly Leu Tyr Gln Gly Leu Ser Thr Ala Thr Lys Asp Thr Tyr Asp
        835                 840                 845

Ala Leu His Met Gln Ala Leu Pro Pro Arg
    850                 855

<210> SEQ ID NO 36
<211> LENGTH: 402
<212> TYPE: PRT
<213> ORGANISM: Artificial Sequence
<220> FEATURE:
<223> OTHER INFORMATION: Inducible Caspase 9 (iCasp9) sequence

<400> SEQUENCE: 36

Met Leu Glu Gly Val Gln Val Glu Thr Ile Ser Pro Gly Asp Gly Arg
1               5                   10                  15

```
Thr Phe Pro Lys Arg Gly Gln Thr Cys Val His Tyr Thr Gly Met
             20                  25                  30

Leu Glu Asp Gly Lys Lys Val Asp Ser Ser Arg Asp Arg Asn Lys Pro
         35                  40                  45

Phe Lys Phe Met Leu Gly Lys Gln Glu Val Ile Arg Gly Trp Glu Glu
 50                  55                  60

Gly Val Ala Gln Met Ser Val Gly Gln Arg Ala Lys Leu Thr Ile Ser
 65                  70                  75                  80

Pro Asp Tyr Ala Tyr Gly Ala Thr Gly His Pro Gly Ile Ile Pro Pro
                 85                  90                  95

His Ala Thr Leu Val Phe Asp Val Glu Leu Leu Lys Leu Glu Ser Gly
             100                 105                 110

Gly Gly Ser Gly Val Asp Gly Phe Gly Asp Val Gly Ala Leu Glu Ser
         115                 120                 125

Leu Arg Gly Asn Ala Asp Leu Ala Tyr Ile Leu Ser Met Glu Pro Cys
130                 135                 140

Gly His Cys Leu Ile Ile Asn Asn Val Asn Phe Cys Arg Glu Ser Gly
145                 150                 155                 160

Leu Arg Thr Arg Thr Gly Ser Asn Ile Asp Cys Glu Lys Leu Arg Arg
                165                 170                 175

Arg Phe Ser Ser Leu His Phe Met Val Glu Val Lys Gly Asp Leu Thr
                180                 185                 190

Ala Lys Lys Met Val Leu Ala Leu Leu Glu Leu Ala Gln Gln Asp His
            195                 200                 205

Gly Ala Leu Asp Cys Cys Val Val Ile Leu Ser His Gly Cys Gln
        210                 215                 220

Ala Ser His Leu Gln Phe Pro Gly Ala Val Tyr Gly Thr Asp Gly Cys
225                 230                 235                 240

Pro Val Ser Val Glu Lys Ile Val Asn Ile Phe Asn Gly Thr Ser Cys
                245                 250                 255

Pro Ser Leu Gly Gly Lys Pro Lys Leu Phe Phe Ile Gln Ala Cys Gly
                260                 265                 270

Gly Glu Gln Lys Asp His Gly Phe Glu Val Ala Ser Thr Ser Pro Glu
            275                 280                 285

Asp Glu Ser Pro Gly Ser Asn Pro Glu Pro Asp Ala Thr Pro Phe Gln
        290                 295                 300

Glu Gly Leu Arg Thr Phe Asp Gln Leu Asp Ala Ile Ser Ser Leu Pro
305                 310                 315                 320

Thr Pro Ser Asp Ile Phe Val Ser Tyr Ser Thr Phe Pro Gly Phe Val
                325                 330                 335

Ser Trp Arg Asp Pro Lys Ser Gly Ser Trp Tyr Val Glu Thr Leu Asp
                340                 345                 350

Asp Ile Phe Glu Gln Trp Ala His Ser Glu Asp Leu Gln Ser Leu Leu
                355                 360                 365

Leu Arg Val Ala Asn Ala Val Ser Val Lys Gly Ile Tyr Lys Gln Met
            370                 375                 380

Pro Gly Cys Phe Asn Phe Leu Arg Lys Lys Leu Phe Phe Lys Thr Ser
385                 390                 395                 400

Ala Ser
```

<210> SEQ ID NO 37
<211> LENGTH: 157
<212> TYPE: PRT

<213> ORGANISM: Artificial Sequence
<220> FEATURE:
<223> OTHER INFORMATION: Novel marker/suicide gene RQR8 sequence

<400> SEQUENCE: 37

```
Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
            35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
                100                 105                 110

Asp Phe Ala Cys Asp Ile Tyr Ile Trp Ala Pro Leu Ala Gly Thr Cys
            115                 120                 125

Gly Val Leu Leu Leu Ser Leu Val Ile Thr Leu Tyr Cys Asn His Arg
    130                 135                 140

Asn Arg Arg Arg Val Cys Lys Cys Pro Arg Pro Val Val
145                 150                 155
```